US010365218B2

(12) United States Patent
Santori et al.

(10) Patent No.: US 10,365,218 B2
(45) Date of Patent: Jul. 30, 2019

(54) SYSTEMS AND METHODS FOR 4-D HYPERSPECTRAL IMAGING

(71) Applicant: Verily Life Sciences LLC, Mountain View, CA (US)

(72) Inventors: Charles Santori, Palo Alto, CA (US); Supriyo Sinha, Menlo Park, CA (US); Cheng-Hsun Wu, Mountain View, CA (US); James Higbie, Palo Alto, CA (US); Seung Ah Lee, Menlo Park, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 58 days.

(21) Appl. No.: 15/607,457

(22) Filed: May 27, 2017

(65) Prior Publication Data

US 2017/0343477 A1 Nov. 30, 2017

Related U.S. Application Data

(60) Provisional application No. 62/342,252, filed on May 27, 2016.

(51) Int. Cl.
*G01N 21/64* (2006.01)
*G01J 3/18* (2006.01)
(Continued)

(52) U.S. Cl.
CPC ....... *G01N 21/6486* (2013.01); *A61B 5/0071* (2013.01); *A61B 5/0075* (2013.01);
(Continued)

(58) Field of Classification Search
CPC ............ A61B 5/0071; G01N 21/6486; G01N 21/6458; G01N 21/6445;
(Continued)

(56) References Cited

U.S. PATENT DOCUMENTS

| 5,591,981 A | 1/1997 | Heffelfinger et al. |
| 6,859,275 B2 * | 2/2005 | Fateley ..................... G01J 3/02 356/310 |

(Continued)

FOREIGN PATENT DOCUMENTS

| EP | 0916981 A1 | 5/1999 |
| EP | 2720075 A1 | 4/2014 |

(Continued)

OTHER PUBLICATIONS

Qing Ye et al., "High-efficiency electrically tunable phase diffraction grating based on a transparent lead magnesium niobate-lead titanite electro-optic ceramic", Optics Letters, Optical Society of America, vol. 36, No. 13, Jul. 1, 2011, pp. 2453-2455.

(Continued)

*Primary Examiner* — Maurice C Smith
(74) *Attorney, Agent, or Firm* — Kilpatrick Townsend & Stockton LLP

(57) ABSTRACT

Systems and methods for hyperspectral imaging are described. In one implementation, a hyperspectral imaging system includes a sample holder configured to hold a sample, an illumination system, and a detection system. The illumination system includes a light source configured to emit excitation light having one or more wavelengths, and a first set of optical elements that include a first spatial light modulator (SLM), at least one lens, and at least one dispersive element. The illumination system is configured to structure the excitation light into a predetermined two-dimensional pattern at a conjugate plane of a focal plane in the sample, spectrally disperse the structured excitation light in a first lateral direction, and illuminate the sample in an excitation pattern with the one or more wavelengths dispersed in the first lateral direction.

20 Claims, 11 Drawing Sheets

(51) Int. Cl.
| | |
|---|---|
| *G01J 3/44* | (2006.01) |
| *G02B 21/00* | (2006.01) |
| *G02B 21/16* | (2006.01) |
| *A61B 5/00* | (2006.01) |
| *G01J 3/32* | (2006.01) |
| *G01J 3/10* | (2006.01) |
| *G01J 3/28* | (2006.01) |
| *G01J 3/433* | (2006.01) |
| *G01J 3/02* | (2006.01) |
| *G01J 3/12* | (2006.01) |

(52) U.S. Cl.
CPC ............ *G01J 3/0224* (2013.01); *G01J 3/0229* (2013.01); *G01J 3/10* (2013.01); *G01J 3/18* (2013.01); *G01J 3/2823* (2013.01); *G01J 3/32* (2013.01); *G01J 3/433* (2013.01); *G01J 3/4406* (2013.01); *G01N 21/6458* (2013.01); *G02B 21/004* (2013.01); *G02B 21/0076* (2013.01); *G02B 21/16* (2013.01); *G01J 2003/1243* (2013.01); *G01N 21/6408* (2013.01); *G01N 21/6445* (2013.01); *G01N 2021/6471* (2013.01); *G01N 2201/0675* (2013.01)

(58) Field of Classification Search
CPC ............ G01N 2201/0675; G01J 3/0229; G01J 3/4406; G01J 2003/2826
See application file for complete search history.

(56) References Cited

U.S. PATENT DOCUMENTS

| | | | |
|---|---|---|---|
| 7,773,218 B2 * | 8/2010 | Brady ................. | G01J 3/02 250/281 |
| 8,233,148 B2 | 7/2012 | Bodkin et al. | |
| 2009/0309049 A1 | 12/2009 | Van Dijk et al. | |
| 2010/0314554 A1 | 12/2010 | Galimberti et al. | |
| 2011/0228267 A1 | 9/2011 | Hayashi | |
| 2012/0069344 A1 | 3/2012 | Liu | |
| 2012/0307247 A1 | 12/2012 | Tan et al. | |
| 2013/0100525 A1 | 4/2013 | Chiang et al. | |
| 2013/0329270 A1 | 12/2013 | Nielsen et al. | |
| 2016/0202178 A1 | 7/2016 | Acosta | |
| 2017/0089837 A1 | 3/2017 | Matsumoto et al. | |
| 2017/0176338 A1 | 6/2017 | Wu et al. | |

FOREIGN PATENT DOCUMENTS

| | | |
|---|---|---|
| GB | 859208 A | 1/1961 |
| JP | S52014417 A | 2/1977 |
| JP | S63101818 A | 5/1988 |
| JP | 2015219501 A | 12/2015 |
| WO | 2016115018 A1 | 7/2016 |

OTHER PUBLICATIONS

Yanli Zhang et al., "High-efficiency, liquid-crystal-based, controllable diffraction grating", Journal of the Optical Society of America, vol. 22, No. 11, Nov. 2005, p. 2510.
Sirleto L. et al., "Electro-Optical Switch and Continuously Tunable Filter Based on a Bragg Grating in a Planar Waveguide With a Liquid Crystal Overlayer", Optical Engineering, Soc. of Photo-Optical Instrumentation Engineers, vol. 41, No. 11, Nov. 2002, pp. 2890-2898.
International Search Report of International Application No. PCT/US2016/067684 dated Mar. 9, 2017.
International Search Report of International Application No. PCT/US2017/027510 dated Jul. 7, 2017.
Cha et. al., "Nontranslational three-dimensional profilometry by chromatic confocal microscopy with dynamically configurable micromirror scanning", Applied Optics, vol. 39, No. 16, Jun. 1, 2000.
Chakrova et al., "Development of a DMD-based fluorescence microscope", SPIE, 2015.
Diem et al., "Molecular pathology via IR and Raman spectral imaging", Journal of Biophotonics, 6, No. 11-12, pp. 855-886, 2013.
Akbari et al., "Hyperspectral imaging and quantitative analysis for prostate cancer detection", Journal of Biomedical Optics, vol. 17(7), Jul. 2012.
Lu et al., "Medical hyperspectral imaging: a review", Journal of Biomedical Optics, vol. 19(1), Jan. 2014.
Panasyuk et al., "Medical hyperspectral imaging to facilitate residual tumor identification during surgery", Cancer Biology & Therapy, Mar. 1, 2007.
Schultz et al., "Hyperspectral Imaging: A Novel Approach for Microscopic Analysis", Cytometry 43:239-247, 2001.
Bodkin et al., "Snapshot Hyperspectral Imaging—the Hyperpixel Array Camera", Proc. of SPIE, vol. 7334, Apr. 2009.
Zheng et al., "Optical Scatter Imaging with a digital micromirror device", Optics Express, vol. 17, No. 22, Oct. 26, 2009.
De Beule et al., "A Generation-3 Programmable Array Microscope with Digital Micro-Mirror Device", vol. 98, Issue 3, Supplement 1, p. 178a, Jan. 2010.
International Search Report of International Application No. PCT/US2017/034875 dated Aug. 21, 2017.
International Search Report of International Application No. PCT/US2017/034877 dated Aug. 17, 2017.
International Application No. PCT/US2017/034875, "International Preliminary Report on Patentability", dated Dec. 6, 2018, 10 pages.

* cited by examiner

SYSTEMS AND METHODS FOR 4-D HYPERSPECTRAL IMAGING

CROSS-REFERENCE TO RELATED APPLICATION

This application claims the benefit of and incorporates by reference the content of U.S. Provisional Pat. App. No. 62/342,252, filed May 27, 2016.

BACKGROUND

Technical Field

The present disclosure generally relates to the field of imaging and to microscopy systems and methods. More particularly, and without limitation, the disclosed embodiments relate to systems and methods for hyperspectral imaging through the use of spatial light modulators and dispersive elements.

Background Description

Hyperspectral imaging is a remote-sensing spectroscopic method typically used in non-medical applications, such as in material identification, astronomy, surveillance, and geophysical applications. It is a method of "imaging spectroscopy" that combines the spatial resolution of imaging with the chemical specificity of spectroscopy. Light collected from an object is dispersed into a spectrum of wavelengths or narrow spectral bands, and detected on a two-dimensional (2-D) imaging sensor as a set of images, each image representing one of the wavelengths or spectral bands. Therefore, datasets collected by hyperspectral imaging systems are often referred to as a hyperspectral cube, represented in three-dimensions (3-D): two spatial directions (x direction and y direction) and one spectral dimension (λ).

Hyperspectral imaging is an emerging technology for medical applications, such as in disease diagnosis and surgery. Biological tissues have intrinsic and extrinsic optical signatures, such as endogenous fluorescence and exogenous fluorescence, that can reflect their chemical, biophysical, and/or morphological characteristics. Hyperspectral imaging can be applied to investigate the physiologic and/or pathologic changes in living tissue or tissue slices and further provide information about the health or disease of the tissue. For example, hyperspectral imaging may replace biopsy as a digital pathology tool. Typically, frozen-section biopsy is used for obtaining information about a tissue sample for an oncology surgeon to make decisions during surgery. Such biopsies may take about 10 to 20 minutes and employ quick staining protocols that render poorer feature definition than standard staining methods. By imaging autofluorescence from the tissue sample and resolving the spectral signatures of the autofluorescence, hyperspectral imaging may be applied as a more rapid histopathology analysis tool that could allow for higher diagnostic accuracy over frozen-section biopsies. Additionally, hyperspectral imaging may be applied as an experimental tool for research and clinical studies, such as applications in immunohistochemistry (IHC) staining and fluorescence in situ hybridization (FISH), in which molecules labeled with various fluorophores with different spectral signatures are targeted to specific proteins and nucleic acids.

The information in the spectral dimension of a hyperspectral cube typically reflects the light intensity over a range of wavelengths emitted by fluorophores or other types of optical labels when they are excited at a given wavelength. However, if the light intensity is measured as a function of both the excitation wavelength and the emission wavelength, more precise identification of the optical characteristics of the fluorophores, optical labels, fluorophore-tagged molecules, and/or the biological tissue is possible. In addition, in many medical applications, various types of intrinsic or extrinsic labels having different spectral signatures may be used, including fluorophores, Raman labels, photoluminescence labels, or quantum dots (QD). Measuring the combined excitation and emission spectra may enhance the ability to distinguish, identify, and characterize different labels of a given type or various types of labels.

Acquiring hyperspectral imaging datasets having both excitation and emission spectra would normally be extremely time-consuming because it would be necessary to measure the intensity of emitted light at multiple excitation and emission wavelengths. For example, many widefield 2-D fluorescent images can be acquired with different filters on a collection path, each filter transmitting a narrow spectral band in the emission spectrum. To acquire the additional excitation spectrum, this procedure then needs to be repeated at different excitation wavelengths using many different excitation lasers. Furthermore, most of the collected fluorescence light is discarded if narrowband filters are used one at a time. Thus, such a procedure is inefficient and could even result in photobleaching of the fluorophores in the sample such that they are permanently unable to fluoresce. Therefore, there is a need for rapid, efficient, and automated methods and systems for acquiring hyperspectral imaging datasets with both excitation and emission spectra.

SUMMARY

The embodiments of the present disclosure include systems and methods for achieving hyperspectral imaging that allows for acquiring a hyperspectral-imaging dataset with both excitation and emission spectra. Advantageously, the exemplary embodiments allow for rapid, efficient, and automated acquisition of a four-dimensional (4-D) hyperspectral-imaging dataset, including two spatial dimensions (horizontal direction x and vertical direction y), one excitation spectral dimension ($\lambda_a$), and one emission spectral dimension ($\lambda_b$).

According to an exemplary embodiment of the present disclosure, a hyperspectral imaging system is described. The system may include a sample holder configured to hold a sample, an illumination system, and a detection system.

The illumination system may include a light source configured to emit excitation light having one or more wavelengths and a first set of optical elements. The first set of optical elements may include a first spatial light modulator (SLM), at least one lens, and at least one dispersive element. The illumination system may be configured to structure the excitation light into a predetermined two-dimensional pattern at a conjugate plane of a focal plane in the sample, spectrally disperse the structured excitation light in a first lateral direction, and illuminate the sample in an excitation pattern with the one or more wavelengths dispersed in the first lateral direction.

The detection system may include a two-dimensional imaging device and a second set of optical elements. The second set of optical elements may include at least one lens and at least one dispersive element. The detection system may be configured to spectrally disperse emission light collected from the sample in a second lateral direction and image the spectrally dispersed emission light to the imaging device.

According to a further exemplary embodiment of the present disclosure, a method for hyperspectral imaging is described. The method includes the steps of providing a light source that emits excitation light of one or more wavelengths, structuring, by a first spatial light modulator (SLM), the excitation light from the light source into a predetermined two-dimensional pattern at a conjugate plane of a focal plane in a sample, spectrally dispersing, by a first dispersive element, the structured excitation light in a first lateral direction, illuminating the sample in an excitation pattern with the one or more wavelengths dispersed in the first lateral direction, spectrally dispersing, by a second dispersive element, emission light collected from the sample in a second lateral direction, and imaging the spectrally dispersed emission light to the imaging device.

According to a yet further exemplary embodiment of the present disclosure, a method for configuring a microscope to obtain a hyperspectral-imaging dataset of a sample is described. The method includes the steps of providing a light source that emits excitation light of one or more wavelengths, structuring, by a first spatial light modulator (SLM), the excitation light from the light source into a predetermined two-dimensional pattern at a conjugate plane of a focal plane in the sample, spectrally dispersing, by a first dispersive element, the structured excitation light in a first lateral direction, illuminating the sample in an excitation pattern with the one or more wavelengths dispersed in the first lateral direction, spectrally dispersing, by a second dispersive element, emission light collected from the sample in a second lateral direction, and imaging the spectrally dispersed emission light to the imaging device.

Additional features and advantages of the disclosed embodiments will be set forth in part in the description that follows, and in part will be obvious from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of the disclosed embodiments as set forth in the accompanying claims.

DETAILED DESCRIPTION

Figure 1:
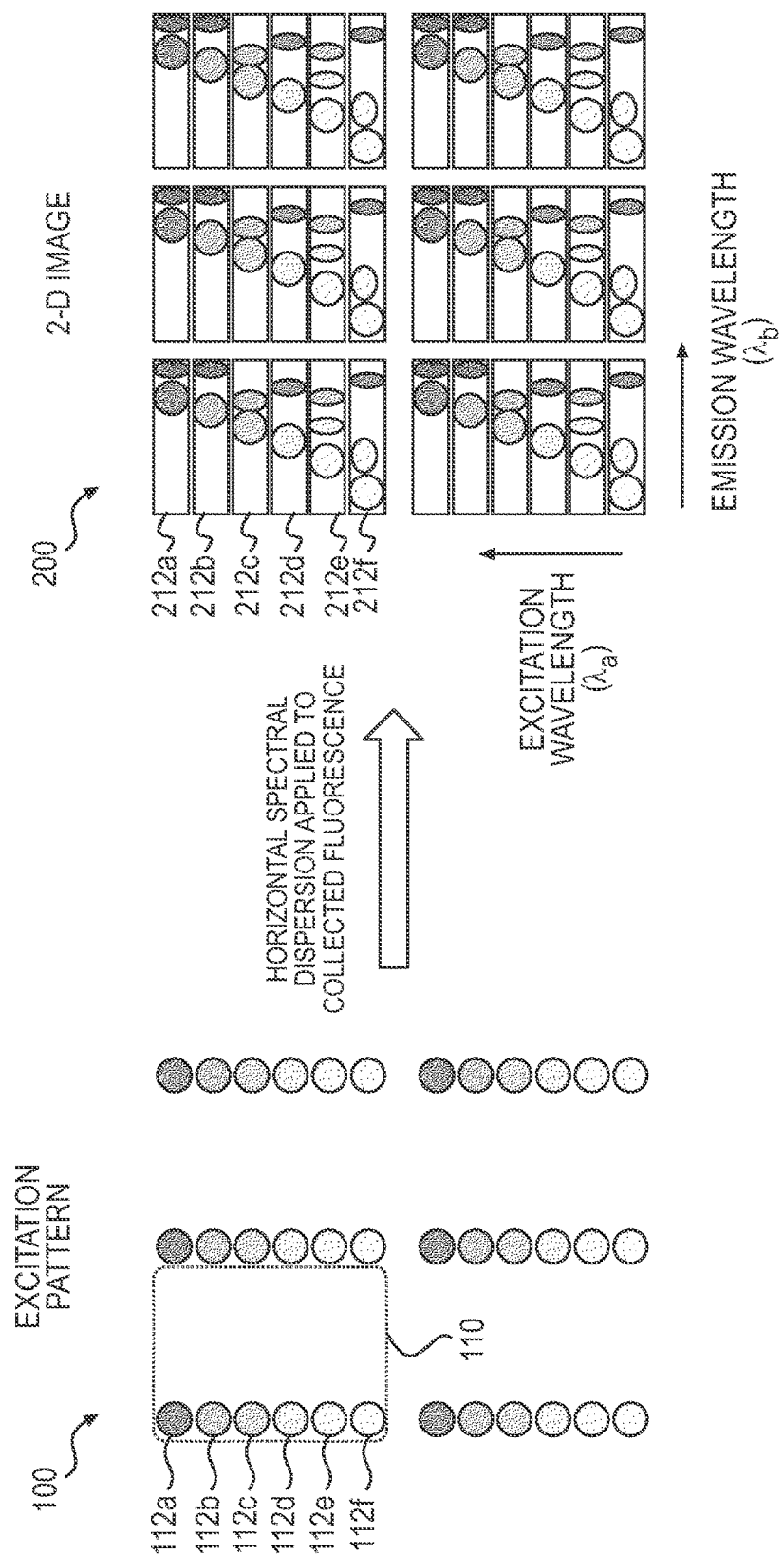
FIG. 1 is a graphical illustration for an exemplary scheme for acquiring a hyperspectral-imaging dataset, according to embodiments of the present disclosure.

The disclosed embodiments relate to systems and methods for achieving hyperspectral imaging that allows for acquiring a hyperspectral-imaging dataset with both excitation and emission spectra. Embodiments of the present disclosure may be implemented using a microscope, such as a fluorescence microscope, a confocal microscope (with confocality along at least one dimension), a transmission microscope, or a reflectance microscope, having one or more 2-D imaging devices, e.g., a CCD or CMOS sensor or camera. Alternatively, an optical system may be built according to embodiments of the present disclosure using suitable optical elements.

Rather than using the time-consuming procedure that acquires a hyperspectral cube for each excitation wavelength, embodiments of the present disclosure allow for acquiring a 2-D image of emission spectra corresponding to more than one excitation wavelengths for a subset of areas on a sample. A plurality of the 2-D images can be acquired and computationally reconstructed to obtain a 4-D hyperspectral-imaging dataset of a sample.

According to an aspect of the present disclosure, excitation light having one or more wavelengths may be used to excite fluorophores in the sample. The excitation light may be generated by a multi-color light source that emits light with one or more wavelengths. In some embodiments, the multi-color light source may have a continuous spectrum. For example, the multi-color light source may be a broadband light source, such as a supercontinuum laser, a white light source (e.g., a high-pressure mercury lamp, a xenon lamp, a halogen lamp, or a metal halide lamp), or one or more LEDs. In other embodiments, the multi-color light source may have a discrete spectrum. For example, the multi-color light source may be a combination of pulsed or continuous "single-wavelength" lasers that emit light with very narrow spectra.

According to an aspect of the present disclosure, excitation light emitted by the light source may be structured for exciting a subset of areas on the sample in an excitation pattern using a spatial light modulator (SLM). To structure the excitation light, the SLM may modulate the phase or amplitude of the excitation light by selectively actuating or switching its pixels. In some embodiments, the SLM may be selected from a group of SLMs including a digital micromirror device (DMD), a diffractive optical element, a liquid crystal device (LCD), and a liquid crystal-on-silicon (LCOS) device.

According to an aspect of the present disclosure, the structured excitation light may be spectrally dispersed in a first lateral direction (e.g., the vertical direction y or the horizontal direction x). Spectral dispersion of the excitation light may separate or split one or more wavelengths of the spectrum of the excitation light in the first lateral direction. In some embodiments, at least one dispersive element may be used to spectrally disperse the excitation light before it illuminates the sample in the excitation pattern. The at least one dispersive element may be a diffractive grating or a prism, or a combination of one or more prisms. Therefore, a spectrally dispersed excitation pattern may be generated to illuminate areas at various spatial locations on the sample.

Fluorophores or other types of optical labels in the sample may be excited by the excitation light illuminating the sample. When they relax to the ground state, the fluorophores or optical labels may emit light in a range of wavelengths known as the emission spectrum. The fluorophores or optical labels may have different emission spectra corresponding to different wavelengths of the excitation light.

As described herein, fluorophores are used in this disclosure as an exemplary optical label. Descriptions in references to fluorophores are equally applicable to other types of optical labels consistent with the embodiments of this disclosure. For example, the excitation light emitted from the light source may also excite other types of optical labels, which upon excitation, may emit light with an emission spectrum. Therefore, fluorescent light and fluorescence emission spectrum used in the descriptions in this disclosure may also be used to represent the emission light and emission spectra of other optical labels.

According to an aspect of the present disclosure, fluorescent light emitted by the fluorophores excited by the excitation light in a given area of the sample may be spectrally dispersed in a second lateral direction (e.g., the horizontal direction x or the vertical direction y). At least one dispersive element may be employed to spectrally disperse the fluorescent light into a fluorescence emission spectrum corresponding to the excitation wavelength at that given area. The fluorescence emission spectra of a subset of areas on the sample may be acquired as a 2-D image in one exposure by the 2-D imaging device.

According to an aspect of the present disclosure, fluorescence excitation and emission spectra of all the areas across the sample or across a field of view may be acquired by scanning the spectrally dispersed excitation pattern in the first and second lateral directions and acquiring a 2-D image of the fluorescence emission spectra at each spatial location of the excitation pattern.

In some embodiments, the excitation pattern is scanned across the sample or the field of view by modulating the pixels of the SLM. In other embodiments, an x-y translation stage may be used to laterally scan the excitation pattern across the sample or the field of view by moving the sample or a diffraction grating in the first and second lateral directions. The stage may be a motorized translation stage, a piezoelectric translation stage, or any suitable stage that allows for lateral linear movement.

Advantageously, the 4-D hyperspectral-imaging dataset may be computationally reconstructed from the 2-D images of the emission spectra, each 2-D image corresponding to the excitation pattern at a different spatial location on the sample.

In some aspects, systems and methods according to the present disclosure allows for confocal optical sectioning. This may allow for acquisition of a hyperspectral-imaging dataset for a plurality of focal planes along an axial direction of the sample. According to an aspect of the present disclosure, a hyperspectral-imaging dataset for a focal plane may be acquired by implementing one or more optical pinholes at a plane conjugate to the selected focal plane. The optical pinholes may be one or more spatial pinholes, or programmable artificial pinholes formed by pixels of a second SLM.

Advantageously, a degree of confocality may be adjusted as needed by changing the size and/or separation of the artificial pinholes formed by the SLM. Additionally, a pinhole pattern may be formed by the SLM by selectively modulating or switching its pixels to match the excitation pattern of the excitation light. The pinhole pattern may advantageously allow for confocal imaging of a plurality of areas on the sample simultaneously illuminated by the excitation pattern. This may increase the speed and/or throughput of acquiring hyperspectral-imaging datasets across the sample at the focal plane comparing to traditional confocal microscopes that use sequential point-by-point scanning.

Reference will now be made in detail to embodiments and aspects of the present disclosure, examples of which are illustrated in the accompanying drawings. Where possible, the same reference numbers will be used throughout the drawings to refer to the same or like parts.

As described herein, to illustrate different wavelengths or frequencies of light, different densities of dotted texture are used in the attached drawings. Higher densities correspond to longer wavelengths or lower frequencies of light. Additionally, vertical and horizontal directions are used as examples for illustrating first and second lateral directions. Alternatively, the horizontal direction may be the first lateral direction and the vertical direction may be the second lateral direction. As described herein, any two suitable different directions or a pair of non-parallel, e.g., orthogonal, directions may be used as first and second lateral directions.

Exemplary Schemes for Acquiring a Hyperspectral-Imaging Dataset

FIG. 1 graphically illustrates an exemplary scheme for acquiring a hyperspectral-imaging dataset used by methods and systems of the present disclosure. As shown in FIG. 1, excitation light having a discrete spectrum is illuminated onto a sample in an excitation pattern 100. Excitation pattern 100 may include a 2-D array of excitation spots. For example, FIG. 1 illustrates a portion of an exemplary 2-D array of circular excitation spots. Additional spots of the array may be located above, below, to the left, and/or to the right of the exemplary array (not shown). As described herein, a suitable size of the array, and a suitable shape, size, and/or separation of the spots may be predetermined according to the application.

The discrete spectrum of the excitation light includes a plurality of discrete wavelengths or a plurality of narrow spectral bands. Thus, when the excitation light is spectrally dispersed by a dispersive element along a given lateral direction, excitation pattern 100 may be spectrally dispersed such that different wavelengths of light are directed to different locations in the given lateral direction. For example, as shown in FIG. 1, excitation pattern 100 may include a plurality of scanning cells 110, e.g., a 2-D array of scanning cells 110. When the excitation light is spectrally dispersed along the vertical direction, each scanning cell 110 may include a plurality of excitation spots 112a, 112b, 112c, 112d, 112e, and 112f vertically offset from one another and corresponding to different excitation wavelengths of the excitation light generated by the spectral dispersion.

The vertical separation between the excitation spots may or may not be uniform, and may be predetermined by various factors, such as the excitation wavelengths, the size of the spots, and the amount of dispersion of the excitation light. The total number of the vertically dispersed excitation spots in scanning cell 110 may depend on the number of discrete wavelengths or narrow spectral bands of the excitation light.

To generate an excitation spectrum of a given spatial location on the sample, spectrally dispersed excitation pattern 100 as shown in FIG. 1 may be scanned in the vertical direction such that the excitation spots corresponding to different excitation wavelengths may be shifted to this given spatial location. For example, when excitation pattern 100 is shifted in the vertical direction, areas in each scanning cell 110 previously illuminated by excitation spots 112a, 112b, 112c, 112d, 112e, and 112f can be illuminated by different ones of these excitation spots. For instance, by shifting excitation pattern 100 over one excitation spot, the areas previously illuminated by excitation spots 112b are illuminated by excitation spots 112a, the areas previously illuminated by excitation spots 112c are illuminated by excitation spots 112b, the areas previously illuminated by excitation spots 112d are illuminated by excitation spots 112c, the areas previously illuminated by excitation spots 112e are illuminated by excitation spots 112d, the areas previously illuminated by excitation spots 112f are illuminated by excitation spots 112e, and the areas previously illuminated by excitation spots 112a are illuminated by excitation spots 112f shifted from scanning cells located above (not shown).

Areas within each scanning cell 110 may be scanned by shifting spectrally dispersed excitation pattern 100 in the vertical and horizontal directions. For example, by shifting excitation pattern 100 over the length of scanning cell 110 in the vertical direction, a given area in scanning cell 110 can be illuminated by the different excitation spots corresponding to the different excitation wavelengths of the light source. By shifting excitation pattern 100 vertically and/or horizontally in a continuous fashion or at predetermined separations (e.g., based on the desired vertical and/or horizontal resolution) over the lengths of scanning cell 110, each given area in scanning cell 110 can be illuminated by the different excitation spots.

As shown in FIG. 1, the excitation spots of excitation pattern 100 are separated in the horizontal direction at a given period. Advantageously, the periodic separation of the excitation spots in the horizontal direction allows for measuring the fluorescence emission spectra of the excited areas on the sample. For example, the emitted fluorescent light from a given area illuminated by an excitation spot can be spectrally dispersed in the horizontal direction without overlapping with that of another area. Therefore, the fluorescence emission spectra of a plurality of areas simultaneously illuminated by the excitation spots can be generated and acquired by a 2-D imaging sensor or device.

FIG. 1 shows a 2-D image 200 of the fluorescence emission spectra with the excitation wavelengths ($\lambda_a$) represented in the vertical direction and the emission wavelengths ($\lambda_b$) represented in the horizontal direction. FIG. 1 graphically illustrates that, in 2-D image 200, areas excited by excitation spots 112a, 112b, 112c, 112d, 112e, and 112f corresponding to different excitation wavelengths may generate different fluorescence emission spectra 212a, 212b, 212c, 212d, 212e, and 212f extending in the horizontal direction and correspondingly offset from one another in the vertical direction. Therefore, a plurality of fluorescence emission spectra can be acquired in 2-D image 200, with each emission spectrum corresponding to an excited spot of excitation pattern 100 at a different spatial location on the sample.

As described above, different areas in each scanning cell 110 may be illuminated by spatially shifting excitation pattern 100 laterally in the vertical and horizontal directions. At each spatial position of excitation pattern 100, fluorescence emission spectra of the illuminated areas can be acquired on 2-D image 200. Therefore, a plurality of 2-D images 200 of fluorescence emission spectra may be acquired corresponding to a series of excitation patterns 100 laterally shifted from one another.

By combining datasets of the acquired 2-D images 200, a fluorescence excitation-emission matrix (EEM) may be acquired for each pixel or spatial location in the 2-D images 200. The fluorescence EEM may record or display fluorescence intensities as a function of a plurality of excitation wavelengths and a range of emission wavelengths. Therefore, a 4-D hyperspectral-imaging dataset of the sample having both the excitation and emission spectra may be collected and reconstructed from the acquired 2-D images 200.

Figure 2:
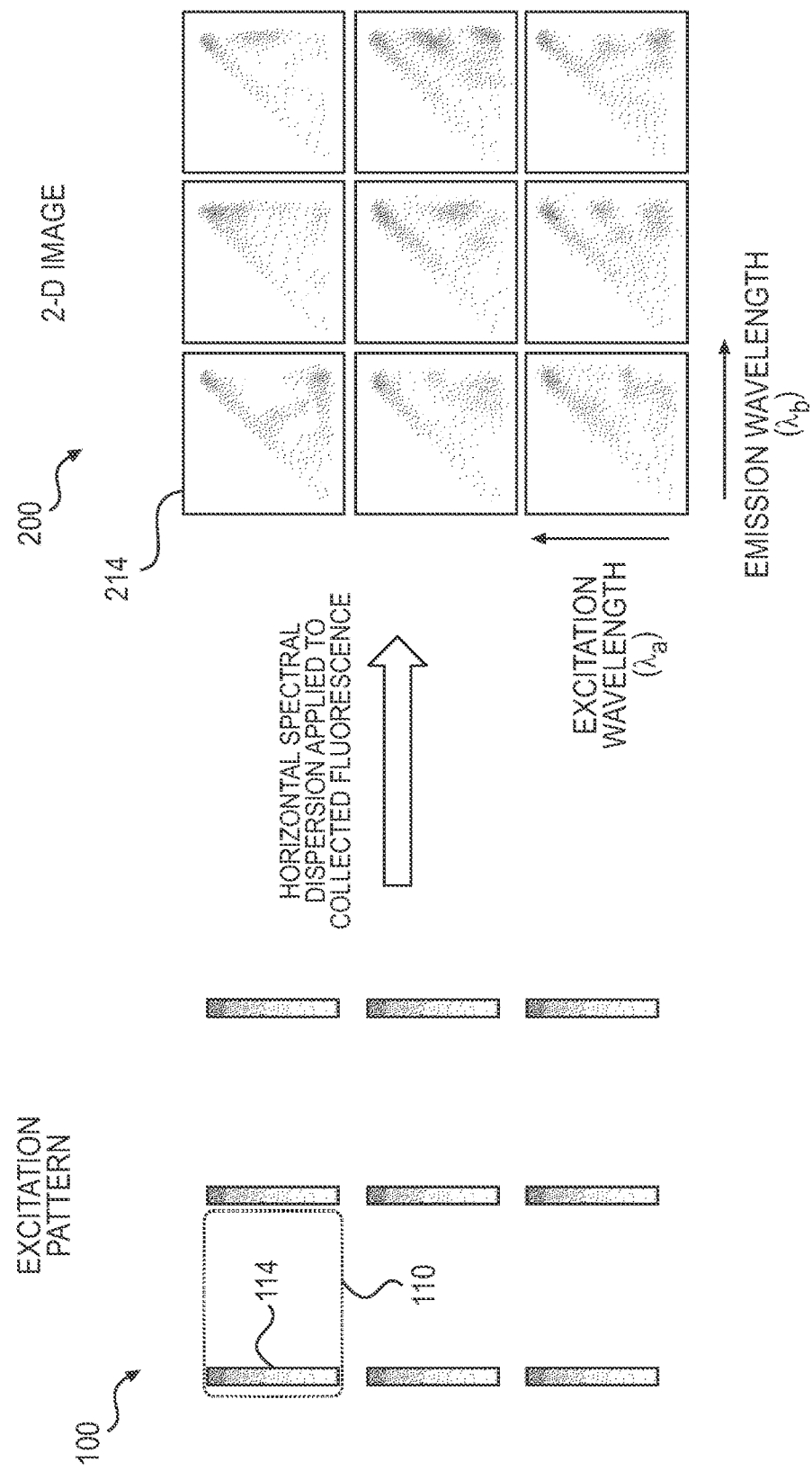
FIG. 2 is a graphical illustration for another exemplary scheme for acquiring a hyperspectral-imaging dataset, according to embodiments of the present disclosure.

FIG. 2 graphically illustrates another exemplary scheme for acquiring a hyperspectral-imaging dataset by methods and systems of the present disclosure. As shown in FIG. 2, when the excitation light has a continuous spectrum and is spectrally dispersed by a dispersive element along the vertical direction, a focused spot of the excitation light may be spectrally dispersed into a continuous excitation line along the vertical direction. In such instances, as shown in FIG. 2, excitation pattern 100 may be spectrally dispersed into a 2-D array of excitation lines 114, each representing the range of wavelengths of the excitation light vertically offset in a continuous fashion.

FIG. 2 illustrates a portion of an exemplary 2-D array of excitation lines 114, which shows a three-by-three 2-D array. Other excitation lines of the array may be located above, below, to the left, and/or to the right of the exemplary array (not shown). As described herein, a suitable size of the array, a suitable shape, size, and/or separation of the excitation lines may be selected according to a given application.

Areas within each scanning cell 110 may be similarly scanned as described above by shifting spectrally dispersed excitation pattern 100 in the vertical and horizontal directions. An array of fluorescence emission spectra 214 corresponding to the array of excitation lines 114 of excitation pattern 100 may be similarly acquired on 2-D image 200. Each fluorescence emission spectrum 214 in 2-D image 200 corresponds to a continuous strip on the sample illuminated by an excitation line 114 of excitation pattern 100.

In the scheme shown in FIG. 2, in some embodiments, when shifting spectrally dispersed excitation pattern 100 in the vertical direction, an area excited at a first wavelength along excitation line 114 may then be excited at a second wavelength longer or shorter than the first wavelength after the vertical shifting. Therefore, by shifting excitation pattern 100 vertically in a continuous fashion or over predetermined separations (e.g., based on the desired vertical resolution), areas illuminated by excitation lines 114 in each scanning cell 110 can be illuminated in the different excitation wavelengths of the light source. Similar to the scheme shown in FIG. 1, other areas on the sample in each scanning cell 110 may be illuminated by the different excitation lines by shifting excitation pattern 100 in the horizontal direction.

As described herein, the areas on the sample illuminated by excitation pattern 100 may be substantially determined by the size and shape of the excitation spots or excitation lines of excitation pattern 100. The size and shape of the excitation spots or excitation lines may be determined by many factors of the optical system, including the size and shapes of the pixels of the SLM, the magnification of the optical system, and the degree of spectral dispersion of the excitation light.

The spatial separation, horizontal and/or vertical, between excitation spots or lines of excitation pattern 100 may be predetermined based on various factors, such as the excitation wavelengths, the size of the sample, the field of view of the optical system, the desired measurement throughput, spatial resolution, and/or speed, and the amounts of spectral dispersion of excitation light and/or emitted fluorescent light.

For example, the spatial separation between the excitation spots or lines in the vertical direction may be predetermined based on the amount of spectral dispersion of the excitation light such that the excitation spots or lines do not overlap in the vertical direction. The spatial separation between the excitation spots or lines in the horizontal direction may be predetermined based on the range of the fluorescence emission spectra in the horizontal direction such that the fluorescence emission spectra do not overlap with each other in the horizontal direction.

In some embodiments, the horizontal and/or vertical periods of an array of excitation spots for different wavelengths may be the same. In other embodiments, the horizontal and/or vertical periods of an array of excitation spots for different wavelengths may be different. Different spatial periods may be convenient for computationally reconstructing the 4-D hyperspectral imaging dataset in some cases, for example, where the SLM is placed at a Fourier plane of the sample to generate excitation pattern 100 as described further below.

Embodiments to be described below in reference to schematic representations of optical systems and/or components are directed to systems and methods for achieving the above-described schemes for acquiring a 4-D hyperspectral-imaging dataset. The schematic representations are to be understood as not being drawn to scale.

Exemplary Optical Systems and Components

Figure 3:
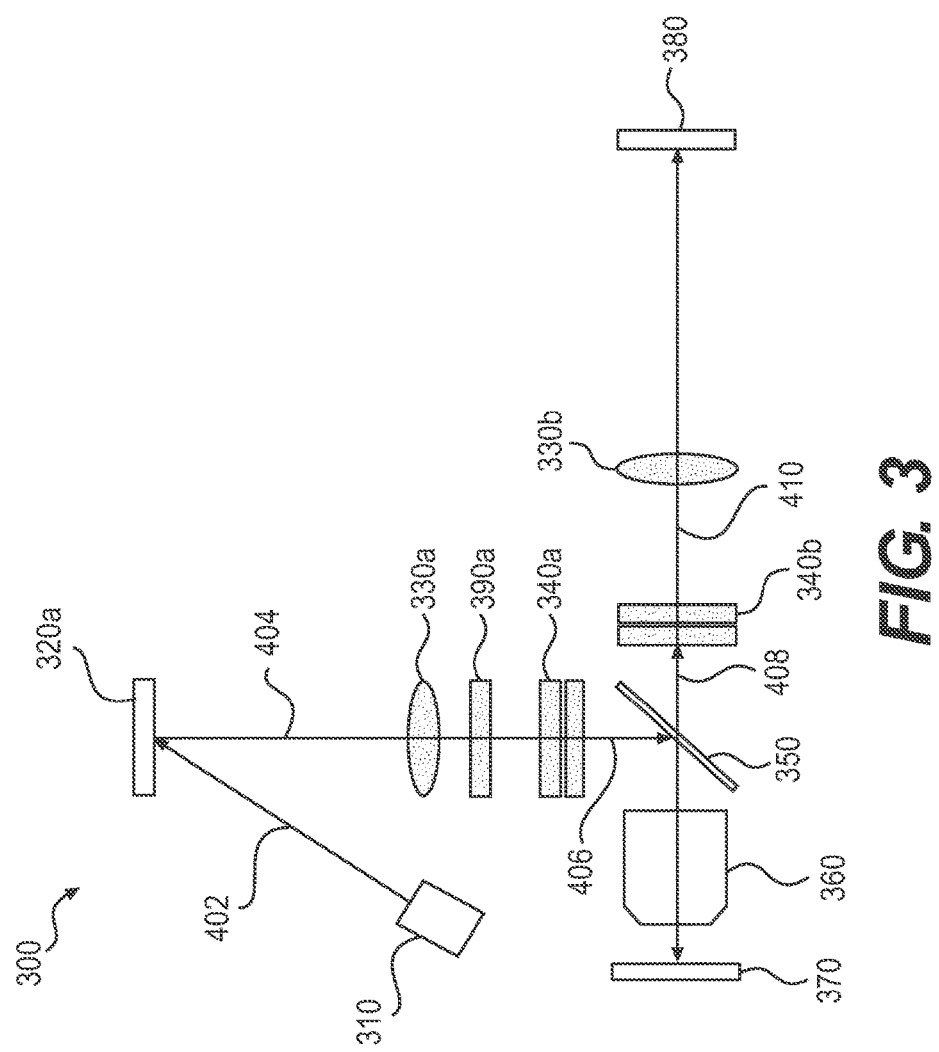
FIG. 3 is a schematic representation of an exemplary hyperspectral imaging system, according to embodiments of the present disclosure.

FIG. 3 is a schematic representation of an exemplary hyperspectral imaging system 300. In some embodiments, system 300 may be a fluorescence microscope, a transmission microscope, or a reflectance microscope, or a confocal fluorescence microscope (with confocality along at least one dimension). Embodiments of the present disclosure are applicable to other suitable microscopy techniques for performing hyperspectral imaging.

As shown in FIG. 3, system 300 may include an illumination system and a detection system, each having a plurality of components. The illumination system may include a light source 310, a first SLM 320a, at least one lens, e.g., lens 330a, and at least one dispersive element, e.g., dispersive element 340a. The detection system may include a 2-D imaging device 380, at least one lens, e.g., lens 330b, and at least one dispersive element, e.g., dispersive element 340b. Depending on its layout, geometry, and/or application, system 300 may further include a beamsplitter 350, an objective 360, a polarizer 390a, and/or a sample holder 370 where a sample to be imaged is placed. System 300 may further include other optical elements, such as mirrors, beam dumps, etc.

As described herein, an optical axis of system 300 may define a path along which the excitation light and emitted fluorescent light from the sample propagate through system 300.

In the illumination system, as shown in FIG. 3, light source 310 emits excitation light 402, which is directed to SLM 320a. Excitation light 402 may be collimated and/or expanded using one or two lenses (not shown). SLM 320a may structure excitation light 402 through modulating the phase or amplitude of excitation light 402 by selectively actuating or switching its pixels. At least a portion of the pixels of SLM 320a reflect excitation light 402 and direct it along the optical axis of system 300.

As shown in FIG. 3, reflected excitation light 404 transmits through lens 330a and dispersive element 340a. Lens 330a may collimate reflected excitation light 404 along the optical axis. Dispersive element 340a spectrally disperses reflected excitation light 404 along a first lateral direction. For example, dispersive element 340a may cause small wavelength-dependent angular deflection to reflected excitation light 404. Spectrally dispersed excitation light 406 may be reflected by beamsplitter 350 and directed towards objective 360. Objective 360 then focuses spectrally dispersed excitation light 406 to a sample placed on sample holder 370.

In the detection system, as shown in FIG. 3, fluorescent light emitted by excited fluorophores in the sample is collected and/or collimated by objective 360. Fluorescent light 408 transmits through beamsplitter 350 and dispersive element 340b along the optical axis of system 300. Dispersive element 340b spectrally disperses fluorescent light 408 along a second lateral direction as described above. Spectrally dispersed fluorescent light 410 transmits through lens 330b and is acquired by 2-D imaging device 380. Imaging device 380 may be placed about one focal length away from lens 330b such that lens 330b may image and focus the spectrally dispersed fluorescent light 410 onto a 2-D sensor of imaging device 380.

Other configurations of system 300 are possible using additional optical elements, such as mirrors, lenses, etc., as further described below.

Functions and the working principles of various components of system 300 are described in detail below.

Light Source

As described above, light source 310 may have a continuous spectrum or a discrete spectrum. Light source 310 may be a white light source, such as a supercontinuum laser, or a combination of "single-wavelength" lasers with discrete narrow spectral bands. In some embodiments, excitation light 402 emitted by light source 310 may be directed straight towards SLM 320a. In other embodiments, excitation light 402 may be collimated and/or expanded by lenses before being incident on SLM 320a. Additionally or alternatively, excitation light 402 may be diffused using a diffuser or a despeckling element to reduce the speckle effect of coherent illumination.

In some embodiments, light source 310 may be operably connected to a controller (not shown) having a processor and a computer-readable medium that stores instructions or operational steps. These instructions or steps, when executed by the processor, modulate the operational states of light source 310. For example, the processor may activate or deactivate light source 310, modulate the duration of a pulse when light source 310 is a pulsed light source, and/or switch or tune the emission wavelengths of light source 310.

Spatial Light Modulator for Modulating Excitation Light

As described above, to structure excitation light 402 for illuminating the sample in excitation pattern 100, SLM 320a may modulate the amplitude or phase of excitation light 402 by selectively modulating its pixels between operational states.

Amplitude Modulation

In some embodiments, the amplitude of excitation light 402 may be modulated by SLM 320a. For example, SLM 320a may be a digital micromirror device (DMD) having an array of multiple micromirrors (not shown). These mirrors may be individually actuated to switch between two operational positions, an "on" position and an "off" position. When a micromirror is configured to be in the "on" position, excitation light 402 is reflected to propagate along the optical axis as reflected excitation light 404 directed to the sample. When a micromirror is configured to be in the "off" position, excitation light 402 is reflected towards a direction deviated from the optical axis and is not directed to the sample (not shown). In some embodiments, excitation light 402 reflected by the "off" micromirrors may be directed to other optical elements, such as a mirror or a beam dump (not shown).

In some embodiments, the micromirrors are of a square shape having a length of its sides ranging from about a few micrometers to about 10 μm. Other shapes and sizes of the micromirrors are also possible and may be suitably used. The DMD is typically capable of changing or alternating the "on" and "off" positions of the micromirrors very rapidly.

In some embodiments, a single micromirror of the DMD may be referred to as a single pixel. In other embodiments, a plurality of micromirrors may be referred to as a single pixel. For example, a group of immediately adjacent micromirrors may be referred as a single pixel and may be modulated or actuated to the same position.

An amplitude modulation pattern may be formed by the micromirrors or pixels of the DMD in the "on" position. The amplitude modulation pattern may be imaged onto the sample as excitation pattern 100 by lens 330a and objective 360. For example, lens 330a is used as a tube lens and combined with objective 360 to form an imaging configuration. The DMD is placed at a conjugate plane to the sample or at about one focal length before lens 330a. Depending on the focal lengths of lens 330a and objective 360, excitation pattern 100 may be a magnified or de-magnified image of the amplitude modulation pattern.

In other embodiments, to modulate the amplitude of excitation light 402, SLM 320a may be a liquid crystal device (LCD) or a liquid crystal-on-silicon (LCOS) device. Pixels of SLM 320a may create an amplitude modulation pattern by manipulating the polarization of light incident on the pixels. Similar to the DMD, the LCD or LCOS device may be placed at a conjugate plane to the sample. Pixels of the LCD or LCOS device may be electrically modulated between an "on" state and an "off" state in a pixel-by-pixel fashion. The "on" pixels may rotate the orientation of linearly polarized light by about 90° while the "off" pixels do not perform the rotation. In such instances, a first linear polarizer (not shown) may be used to linearly polarize excitation light 402. A second linear polarizer or a polarizing beamsplitter (PBS) (not shown) may be used to transmit excitation light 404 reflected by the "on" pixels and block excitation light 402 reflected by the "off" pixels.

A disadvantage of modulating the amplitude of excitation light 402 using SLM 320a is the loss of light during the modulation. This is because most of the pixels of SLM 320a are typically in the "off" state. Accordingly, most of excitation light 402 is steered away from the optical axis and would not reach the sample, and thus is lost. Excitation light recycling systems may be used to reduce this loss by redirecting off-optical axis excitation light back to the optical axis as described further below.

Phase Modulation

Figure 4:
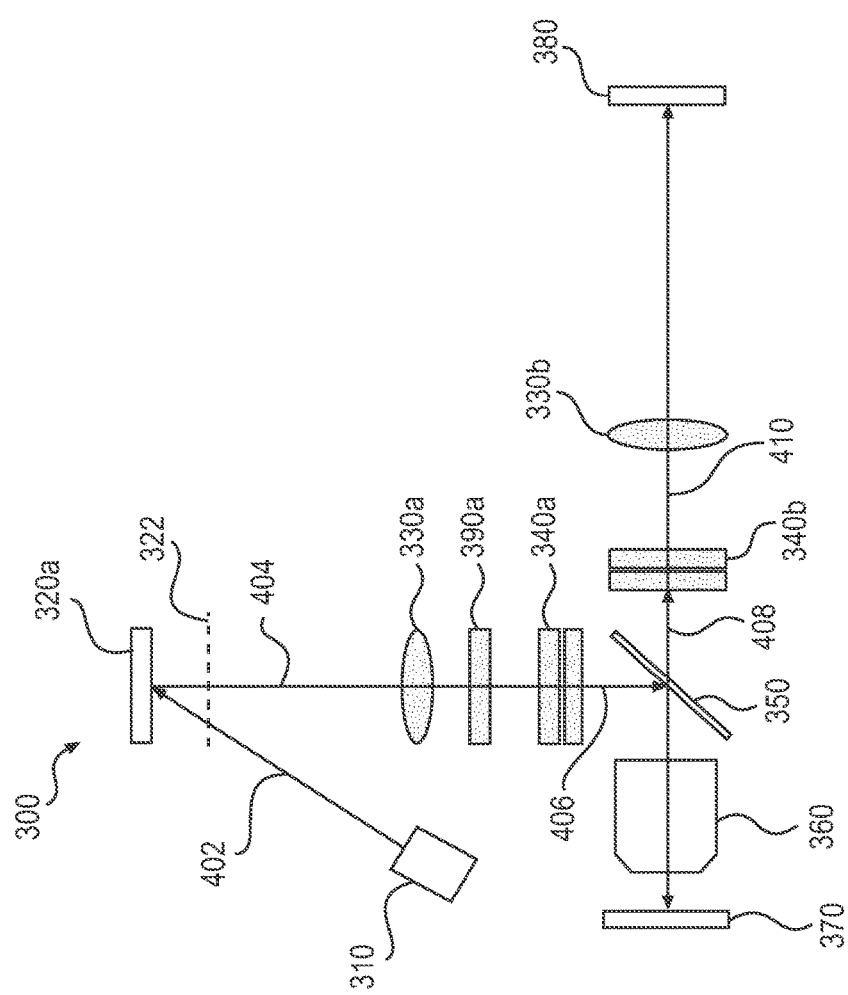
FIG. 4 is a schematic representation of another exemplary hyperspectral imaging system, according to embodiments of the present disclosure.

In some embodiments, the phase of excitation light 402 may be modulated by SLM 320a. SLM 320a may be a reflection type LCD or LCOS device. FIG. 4 is a schematic representation of an exemplary system 300 using a LCD or LCOS device as SLM 320a. As shown in FIG. 4, the LCD or LCOS device may be placed close to a conjugate plane 322 to the sample. A custom phase modulation pattern may be formed by the pixels of the LCD or LCOS device. The phase modulation pattern may create an array of off-axis lens phase profiles. Wavefront of excitation light 402 may then be modulated by the phase modulation pattern and form a preliminary excitation pattern (e.g., a diffraction pattern) at conjugate plane 322. This preliminary excitation pattern may be a magnified or de-magnified image of excitation pattern 100 and may include an array of focused spots.

Conjugate plane 322 may be located a short distance beyond SLM 320a. The focal plane of the focused spots of the preliminary excitation pattern may be wavelength dependent. Therefore, different wavelengths of excitation light 402 may not all focus on conjugate plane 322. In some embodiments, the focal plane for the center wavelength of excitation light 402 is approximately at conjugate plane 322. The preliminary excitation pattern formed at or close to conjugate plane 322 is then imaged onto the sample as excitation pattern 100 by lens 330a and objective 360. Although different wavelengths of excitation pattern 100 in this configuration may have slightly different focal planes, modulating the phase of excitation light 402 increases the efficiency of using excitation light 402 comparing to amplitude modulation.

In other embodiments, the LCD or LCOS device may be placed at an aperture plane, which may be a conjugate plane to the back aperture of objective 360 or a Fourier plane to the sample. For example, one exemplary configuration of system 300 may have two tube lenses (not shown) placed between SLM 320a and objective 360. A first tube lens may be located about one focal length behind SLM 320a. A second tube lens may be located about two focal lengths behind the first tube lens. Objective 360 may be located about one focal length behind the second tube lens.

The pixels of the LCD or LCOS device may form a custom phase modulation pattern to modulate the wavefront of excitation light 402. Upon the reflection of excitation light 402 by the LCD or LCOS device, phases at different locations of the wavefront of the reflected excitation light 404 may be selectively changed according to the phase modulation pattern. In some embodiments, pixels of the LCD or LCOS device may be electrically modulated between an "on" state and an "off" state in a pixel-by-pixel fashion. If pixels of the LCD or LCOS device are in the "on" state, they may change the phase of the reflected light by changing the optical path length of light traveled in the liquid crystal; and if they are in the "off" state, they may not change the phase of the reflected light. This allows the phase modulation pattern formed by the pixels to be digitally customized as needed. In other embodiments, pixels of the LCD or LCOS device may have multiple states or levels of adjustment (e.g., 256 levels) and may be individually modulated to desired states or levels. Advantageously, increasing the states or levels of adjustment of the pixels increases the continuity of the adjustment of the phase modulation pattern and thus the adjustment of the phase of excitation light 402.

The phase modulation may render wavelets of reflected excitation light 404 having different directions and/or phases. As reflected excitation light 404 propagates along the optical axis, each of the tube lenses and objective 360 may perform Fourier Transform on the wavefront of reflected excitation light 404. A diffraction pattern may then be formed at the focal plane of objective 360. This diffraction pattern is referred to herein as excitation pattern 100 when illuminated on the sample.

In the above-described configuration, because the phase modulation pattern is at or approximately at a Fourier plane to the sample, the phase modulation pattern is the inverse Fourier transform of a desired excitation pattern 100 illuminated on the sample. Because Fourier Transform includes a scaling factor proportional to the wavelength of light, the spatial periods of the array of excitation spots for different wavelengths in excitation pattern 100 may be different. For example, longer wavelength would diffract at larger angles, which can be converted to larger spatial periods. This may cause the corresponding fluorescence emission spectra arrays acquired in 2-D image 200 to have different spatial periods. Customized computer algorithms may be used for generating time-varying phase modulation patterns for scanning across the field of view and/or for computationally reconstructing the 4-D hyperspectral-imaging dataset from datasets of such 2-D images.

Advantageously, modulating the phase of excitation light 402 may allow it to propagate with substantially uniform intensity in the near field of the LCD or LCOS device and thus reduce loss of light. The modulated excitation light may then form customizable or programmable excitation pattern 100 on the sample in the far field. Therefore, comparing to modulating the amplitude of excitation light 402 as described above, modulating the phase of excitation light 402 to create excitation pattern 100 may substantially increase the efficiency of illumination of system 300 by reducing loss of excitation light 402. Additionally, increasing the continuity of the phase modulation of excitation light 402 may further increase the diffraction efficiency of the LCD or LCOS device and thus the efficiency of illumination of system 300.

The LCD or LCOS device for modulating the amplitude or phase of excitation light 402 may alternatively be a transmission type device implemented along the optical axis. The geometry of the illumination system may be suitably designed such that the amplitude or phase modulation pattern formed by the pixels of the device may modulate the amplitude or phase of excitation light 402 similarly as described above.

Whether SLM 320a modulates the amplitude or phase of excitation light 402, excitation pattern 100 can be programmed and customized as needed by modulating pixels of SLM 320a between two or multiple operational states or levels in a pixel-by-pixel fashion. Further, excitation pattern 100 can be translated or shifted in a given spatial direction, such as the horizontal or vertical direction, by scanning or shifting the modulation of the pixels of SLM 320a. This advantageously allows for scanning excitation pattern 100 across the field of view of system 300 without moving the sample and/or sample holder 370 using an x-y translation stage.

In some embodiments, depending on the type and modulation features of the pixels of SLM 320a, excitation light 402 may be directed towards SLM 320a at a predetermined angle relative to a plane of SLM 320a. The predetermined angle may depend on the type of SLM 320a and/or the geometry of system 300. In some instances, when SLM 320a is a reflection type SLM that modulates the phase of excitation light 402, excitation light 402 may be directed towards SLM 320a at an angle such that reflected excitation light 404 propagates along the optical axis of system 300. In other instances, when SLM 320a is a DMD, excitation light 402 may be directed towards the DMD at an angle such that excitation light 404 reflected by the "on" micromirrors propagates along the optical axis.

In some embodiments, SLM 320a may be operably connected to a controller (not shown) having a processor and a computer-readable medium that stores instructions or operational steps. These instructions or steps, when executed by the processor, modulate the operational states of the pixels of SLM 320a to form a desired excitation pattern 100 and/or to translate excitation pattern 100 in a desired spatial direction over a predetermined distance across the field of view.

Lenses and Objective

Various lenses of system 300, such as lenses 330a and 330b, may be achromatic, such as achromatic doublets or triplets, to limit or reduce the effects of chromatic and/or spherical aberration of the system. Further, objective 360 of system 300 may be achromatic. Alternatively or additionally, objective 360 may be an infinity-corrected objective such that objective 360 may form a desired focus (e.g., focused spots or focused pattern) of a collimated light beam entering from its back aperture. Using achromatic lenses and/or achromatic or infinity-corrected objective may allow excitation light 402 of different wavelengths to have at least approximately the same focus in the sample. Further, using achromatic lenses and/or achromatic objective may allow fluorescent light of different wavelengths from a focal plane in the sample to similarly form a focused image at imaging device 380. Therefore, using achromatic lenses and/or achromatic objective may improve the quality of 2-D images 200 of fluorescence emission spectra, and thus the quality of the reconstructed hyperspectral-imaging dataset.

Dispersive Elements

Dispersive elements 340a and 340b may be diffraction gratings or prisms, such as non-deviating prisms (e.g., Amici prisms or double Amici prisms). The types of dispersive elements 340a and 340b may be the same or may be different. The degree of dispersion caused by dispersive elements 340a and 340b may be same or different, and may be predetermined based on various factors, such as the spectral ranges of excitation light and fluorescent light, the size of the sample or the field of view, the size of imaging device 380, the desired spectral resolution, and the application of system 300.

In some embodiments, the degree of dispersion caused by dispersive elements 340a and 340b may be adjustable. For example, dispersive element 340a may be a pair of double Amici prisms placed along the optical axis of system 300. At least one of the pair of double Amici prisms is rotatable relative to the other around the optical axis. The rotation of the double Amici prisms relative to each other may allow for continuous control of the amount and/or angular orientation of the spectral dispersion of excitation light 402. Similarly, dispersive element 340*b* may be a pair of double Amici prisms, allowing for continuous control of the amount and/or angular orientations of the spectral dispersion (e.g., dispersion angles) of fluorescent light 408.

Excitation Light Blocking

Because the intensity of excitation light 402 may be orders of magnitude stronger than fluorescent light 408, excitation light 402 reflected and/or scattered by the sample and/or sample holder 370 may enter the detection system and affect the detection or acquisition of the fluorescence emission spectra by imaging device 380. Therefore, embodiments of the present disclosure may reduce or block excitation light 402 from propagating into the detection system as described below.

In some embodiments, beamsplitter 350 may be used to reject or block excitation light 402 from propagating into the detection system. For example, beamsplitter 350 of system 300 may be a dichroic beamsplitter, a polarizing beamsplitter (PBS), or other suitable type of beamsplitter.

When light source 310 or excitation light 402 has a discrete spectrum having one or more discrete wavelengths or narrow spectral bands, beamsplitter 350 may be a dichroic beamsplitter that selectively reflects and transmits light depending on its wavelength. For example, beamsplitter 350 may be a multiband dichroic that has multiple cut-off wavelengths and passbands. The multiband dichroic may be selected to substantially reflect wavelengths of excitation light 402 and to substantially transmit wavelengths of fluorescent light 408. In such instances, some wavelengths of fluorescent light 408 that are the same or close to that of excitation light 402 may be substantially blocked, and thus may have substantially reduced intensity in 2-D image 200 acquired by imaging device 380.

Alternatively or additionally, when light source 310 or excitation light 402 has a discrete spectrum, a set of corresponding notch filters or a single multi-notch filter (not shown) may be added to the detection system along the optical axis. The notch filters or multi-north filter may selectively reflect the discrete wavelengths or narrow spectral bands of excitation light 402, thereby blocking excitation light 402 from reaching imaging device 380. Again, some wavelengths of fluorescent light 408 that are the same or close to that of excitation light 402 may be substantially blocked by the notch filters, and thus may have substantially reduced intensity in 2-D image 200 acquired by imaging device 380.

When light source 310 or excitation light 402 has a continuous spectrum, beamsplitter 350 may be a long-pass dichroic beamsplitter that reflects at least a portion of the wavelengths of excitation light 402 and transmits at least a portion of the wavelengths of fluorescent light 408. The spectrum of excitation light 402 typically ranges from the ultraviolet through the visible spectra, and the spectrum of fluorescent light 408 typically ranges from the visible into the near infrared spectra. Therefore, the long-pass dichroic beamsplitter may block wavelengths of excitation light 402 and transmit wavelengths of fluorescent light 408. However, in some instances, both the spectrum of excitation light 402 and spectrum of fluorescent light 408 may include short to long wavelengths and they may overlap, e.g., in the visible spectrum. In such instances, the long-pass dichroic beamsplitter may block at least some fluorescent light 408 in the visible spectrum, and may not be suitable for rejecting excitation light 402 in applications where the blocked spectrum of fluorescence light 408 contains desired spectral information, for example.

Regardless of the types of spectrum of light source 310 or excitation light 402 (whether or not discrete or continuous), in some embodiments, polarizer 390*a* and beamsplitter 350 may be used in combination to block excitation light 402 from entering the detection system and thus from propagating towards imaging device 380. For example, beamsplitter 350 may be a polarizing beamsplitter (PBS) that reflects light whose vibration orientation aligns with the transmission axis of polarizer 390*a*.

For example, polarizer 390*a* may be placed at any suitable location along the optical axis to linearly polarize excitation light 402. The PBS may be selected to reflect light having a vibration orientation same as that of the polarized excitation light and to transmit light having a vibration orientation perpendicular to that of the polarized excitation light. Most of the excitation light collected by objective 360 would therefore reflect from this PBS and would not reach imaging device 380. In some instances, both the sample and objective 360 may depolarize reflected and/or scattered excitation light to a small degree, and thus undesirably allow some excitation light to transmit through the PBS and enter the detection system.

2-D Imaging Device

Imaging device 380 may include a suitable 2-D sensor located at an image plane conjugate to a selected focal plane in the sample. The sensor could be implemented with a CMOS sensor, a CCD sensor, a 2-D array of silicon avalanche photodiodes (APDs), an electron-multiplied CCD (EMCCD), an intensified CCD, or other suitable types of 2-D sensors.

Imaging device 380 may be operatively connected to a controller or a computing device (not shown) that controls its operation. For example, controller (not shown) may have a processor and one or more computer-readable medium that stores instructions or operational steps. The instructions or operational steps, when executed by the processor, may operate the exposure of imaging device 380, acquire 2-D images 200, and/or store the datasets of 2-D image 200 to a memory. The computer-readable medium may further store instructions or operational steps that, when executed by the processor, perform data processing of the acquired 2-D image datasets and/or reconstruct the 4-D hyperspectral-imaging dataset from the 2-D image datasets.

System 300 may advantageously have additional technical features and capabilities to enhance its functionality and performance as described in detail below.

Time-Resolved Capability

In some embodiments, time-resolved capability may be advantageously added to system 300 to allow for fluorescence lifetime imaging (FLIM) or time-resolved fluorescence spectroscopy. For example, a pulsed light source, such as a supercontinuum laser, may be used as light source 310, together with a 2-D imaging device 380 having picosecond to nanosecond time-gating capability, such as an intensified CCD camera or an optoelectronic streak camera. Alternatively, a conventional 2-D CCD or CMOS sensor may be used in combination with an electro-optic shutter. In some embodiments, a modulated, electron-multiplied fluorescence lifetime imaging microscope (MEM-FLIM) camera may be used in combination with a modulated light source 310, e.g., a pulsed light source.

The lifetime of the fluorophores or fluorescent molecules in the sample may be calculated from the acquired time-resolved 2-D images of the fluorescence emission spectra for each spatial location in the field of view. This adds another dimension of information to the hyperspectral-imaging dataset, thereby providing additional information about the fluorophores or fluorescent molecules in the sample.

Because FLIM excites the fluorophores with short excitation pulses in the time-domain, the FLIM capability of system 300 may substantially reject the scattered and/or reflected excitation light by discarding the signals close to zero delay. This may advantageously reduce or minimize the effect of the scattered and/or reflected excitation light in the acquired fluorescence signals, e.g., 2-D image 200.

Fluorescence Polarization

In some embodiments, system 300 may advantageously allow for fluorescence polarization (or anisotropy) measurement to obtain additional information about the fluorophores or fluorescent molecules in the sample. Relationships between the polarization of the excitation light and the emitted fluorescent light subsequently detected may be used to analyze and study various chemical and/or physical processes of the molecules in the sample, such as rotational diffusion, binding interactions, and orientation.

Figure 5:
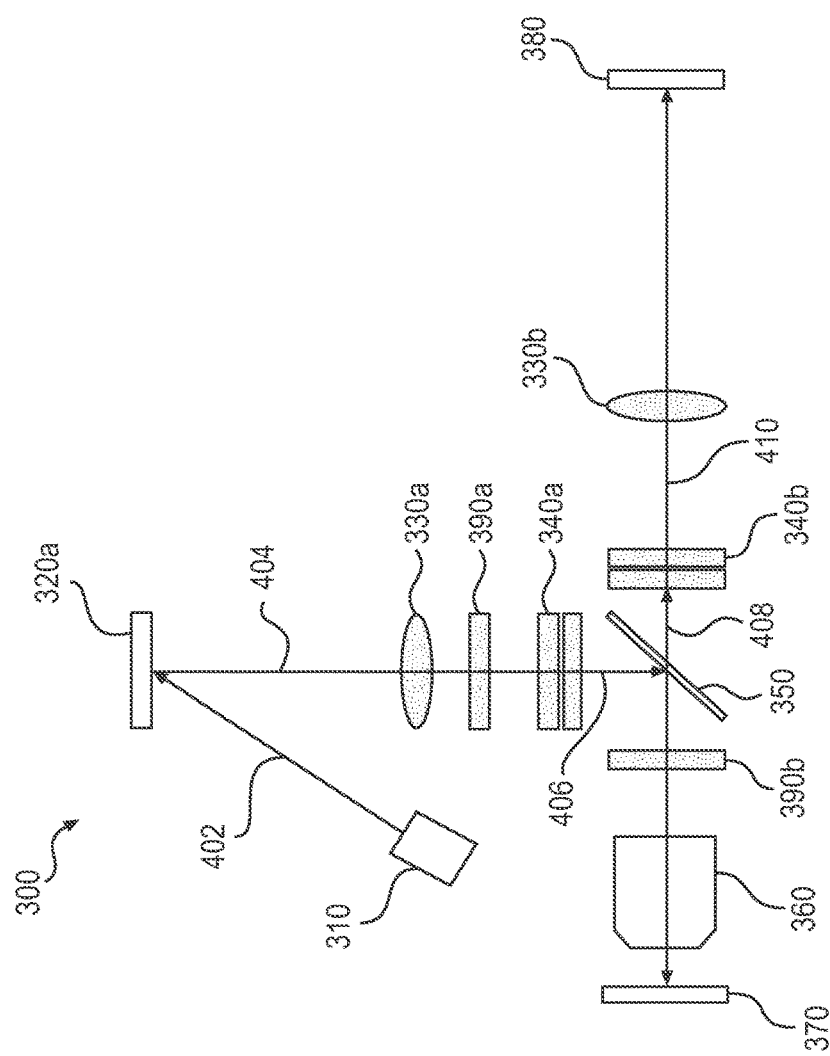
FIG. 5 is a schematic representation of another exemplary hyperspectral imaging system, according to embodiments of the present disclosure.

To add the capability for measuring fluorescence polarization, as shown in FIG. 5, system 300 may include polarizer 390a and an optical element, such as a waveplate or a polarizer. For example, the optical element may be an achromatic half-wave plate (HWP) 390b. Polarizer 390a may be a linear polarizer located in the illumination system, thereby generating linearly polarized excitation light, e.g., vertically polarized light. Depending upon the orientation of their absorption dipoles, individual fluorophores in the sample are preferentially excited by the linearly polarized excitation light. The fluorescent light emitted from the sample may be partially depolarized due to random orientation, diffusion, and/or rotation of the fluorophores.

Beamsplitter 350 may be a polarizing beamsplitter (PBS) that substantially transmits horizontally polarized light and reflects vertically polarized light. For example, as shown in FIG. 5, the excitation light vertically polarized by polarizer 390a can be reflected by the PBS and then propagates towards HWP 390b. HWP 390b may be placed at a suitable location, such as before beamsplitter 350 along the optical axis. In such instances, HWP 390b may rotate the vibration orientations of both the linearly polarized excitation light and the collected fluorescent light from the sample by about twice the angle between a vertical axis and the fast axis of the HWP, for example. Rotating HWP 390b around the optical axis would advantageously rotate the vibration directions of both the excitation light and fluorescent light. Beamsplitter 350 may substantially block the polarized excitation light and transmit at least a portion of polarized fluorescent light to be acquired by imaging device 380.

Depending on the application, such fluorescence polarization assays may be performed in steady state or with time-resolved measurements, such as utilizing the FLIM capability as described above.

Measurement of fluorescence polarization (or anisotropy) adds another dimension of information to the hyperspectral-imaging dataset acquired by system 300. This additional dimension of information may complement the information in the other dimensions of the hyperspectral-imaging dataset about the local chemical and physical environments of fluorophore-tagged molecules in the sample, such as molecular mass and orientation of the molecules. The augmented hyperspectral-imaging dataset acquired by system 300 may further improve the accuracy of diagnosis of physiologic or pathologic changes of the sample.

Excitation Light Recycling System

As described above, because most of excitation light 402 is steered away from the optical axis and would not reach the sample, modulating the amplitude of excitation light 402 using SLM 320a, e.g., a DMD or a LCD, to generate excitation pattern 100 results in loss of light. Therefore, in some embodiments, system 300 may advantageously include an excitation light recycling system 500 to increase efficiency of utilization of excitation light 402. Recycling system 500 may redirect the off-optical axis excitation light back to the optical axis towards the sample as described below.

Reflection-Based Scheme

Figure 6:
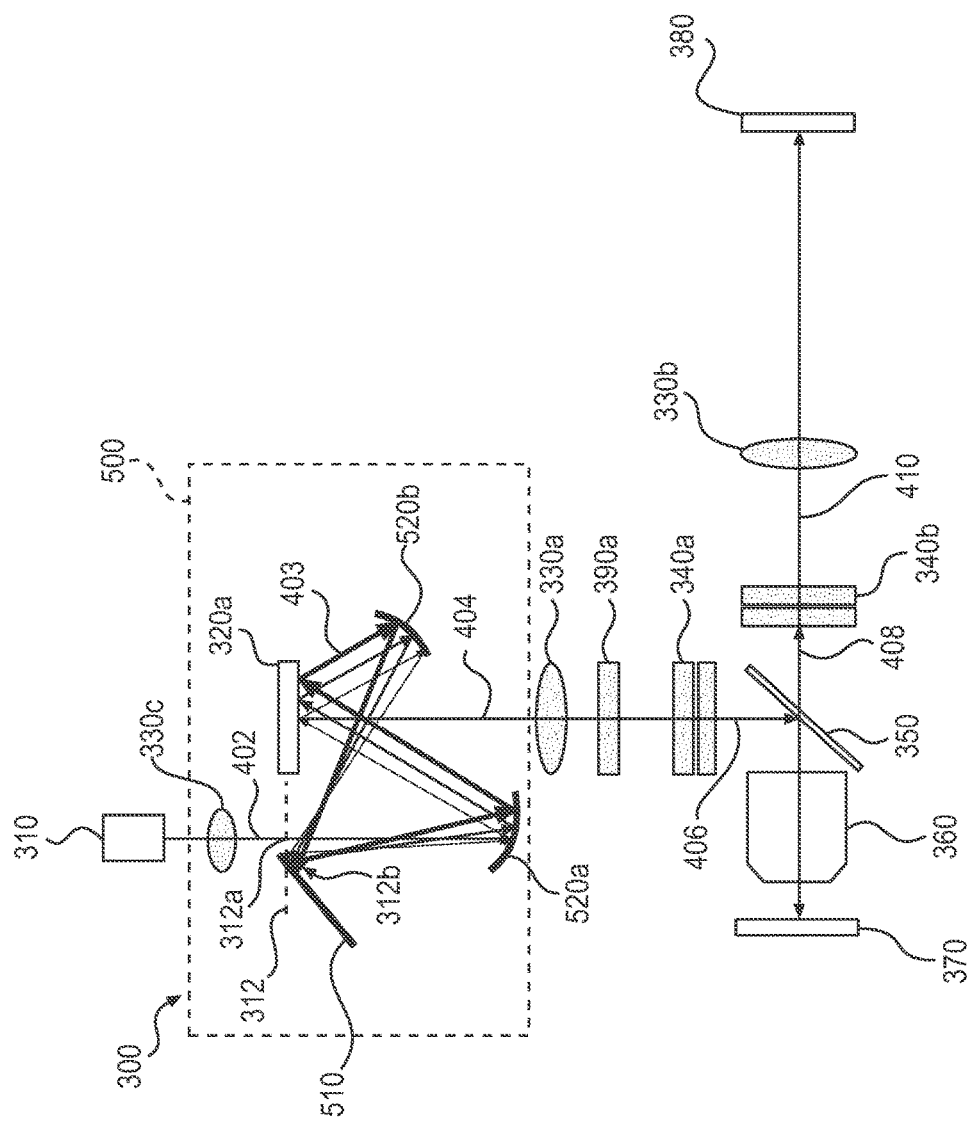
FIG. 6 is a schematic representation of another exemplary hyperspectral imaging system, according to embodiments of the present disclosure.

In some embodiments, excitation light recycling system 500 uses a reflection-based scheme as shown in FIG. 6. Recycling system 500 may include one or more lenses and mirrors. For example, recycling system 500 may include a lens 330c, a flat mirror 510, a first concave mirror 520a, and a second concave mirror 520b. The concave mirrors may be replaced by a combination of a flat mirror and a lens.

Excitation light 402 may be collimated before passing lens 330c. Lens 330c may focus collimated excitation light 402 to a focal point 312a of mirror 520a at a given plane 312 near or aligned with the plane of SLM 320a. Then, excitation light 402 expands as it propagates from focal point 312a to mirror 520a. Mirror 520a may re-collimate excitation light 402 and direct it to SLM 320a.

As described above, when SLM 320a is a DMD, a small fraction of excitation light 402 may be reflected by the "on" pixels towards lens 330a along the optical axis, while the rest, e.g., off-axis excitation light 403, is reflected by the "off" pixels at a different angle and away from the optical axis. Mirror 520b may be configured to intercept this off-axis excitation light 403 and reflect it back to a point 312b very close to focal point 312a. The separation between point 312b and focal point 312a may be just large enough to allow the edge of mirror 510 to intercept the returned off-axis excitation light 403 without substantially blocking the original excitation light 402. Mirror 510 then may direct off-axis excitation light 403 back to SLM 320a via a path that is nearly aligned with the original path. In such configuration, excitation light 402 can be incident onto SLM 320a many times through multiple reflections between the mirrors, thereby recycling off-axis excitation light 403 back to the optical axis.

As described herein, the three paths for the recycling of off-axis excitation light 403 shown in FIG. 6 are exemplary only. Multiple or infinite recycling paths may be possible.

A few design considerations of system 300 are discussed in the following. In some instances, the recycled off-axis excitation light 403 may be slightly divergent. For each recycling path of off-axis excitation light 403 propagating in recycling system 500, because off-axis excitation light 403 is not returned to focal point 312a, off-axis excitation light 403 would have a slightly different angle when it reaches SLM 320a from that of the original excitation light 402. The angular difference (or divergent angle) may be defined as $\Delta\theta = \Delta x/f$, where "$\Delta x$" is the separation between focal point 312a and point 312b, and "f" is the focal length of mirror 520a (or a lens) for re-collimating the off-axis excitation light reflected by mirror 510. $\Delta x$ may be at least greater than any unusable rough edge of mirror 510, and greater than the diffraction limited spot size of excitation light 402. Depending on the values of $\Delta x$ and f, $\Delta\theta$ may be less than 1 degree. Such small degree of angular difference (or divergence angle) may not affect the formation of excitation pattern 100.

In some instances, when SLM 320a is a DMD, the DMD may have a diffraction effect on reflected excitation light 404. For example, a single micromirror of the DMD may have a side length of approximately 10 µm. A typical divergence angle for reflected excitation light 404 caused by the diffraction of the micromirror array may be about $\lambda_a/10$ μm, where $\lambda_a$ is the wavelength of excitation light 402. Therefore, the divergence angle may be about less than one radian, e.g., 1/20 radian, or less than a few degrees, e.g., 3 degrees. Thus, most of excitation light 404 reflected by the "on" pixels or micromirrors of the DMD from different recycling paths in recycling system 500 may overlap and propagate along the optical axis, and thus may not affect the formation of excitation pattern 100.

In some instances, reflected excitation light 404 from different recycling paths in recycling system 500 may exhibit optical interference. For a light source 310 having discrete wavelengths or narrow spectral bands, this interference may cause reflected excitation light 404 to have unstable intensities when focused on the sample. Additional optical components may be added to control the relative phases of excitation light 403 propagating in different recycling paths to reduce the optical interference effect. However, this may complicate the design of system 300. Therefore, the reflection-based scheme shown in FIG. 6 for recycling system 500 may be more suitable for systems 300 having a light source 310 with a broadband spectrum, such as a white light source. For such systems 300, the effect of the interference may impose very rapid small oscillations on the spectrum of reflected excitation light 404. Fluorophores typically have spectrally broad absorption features, allowing these oscillations to average out during excitation. Therefore, the optical interference effect may have little effect on the acquired fluorescence emission spectra when light source 310 has a broadband spectrum.

Polarization-Based Scheme

Figure 7:
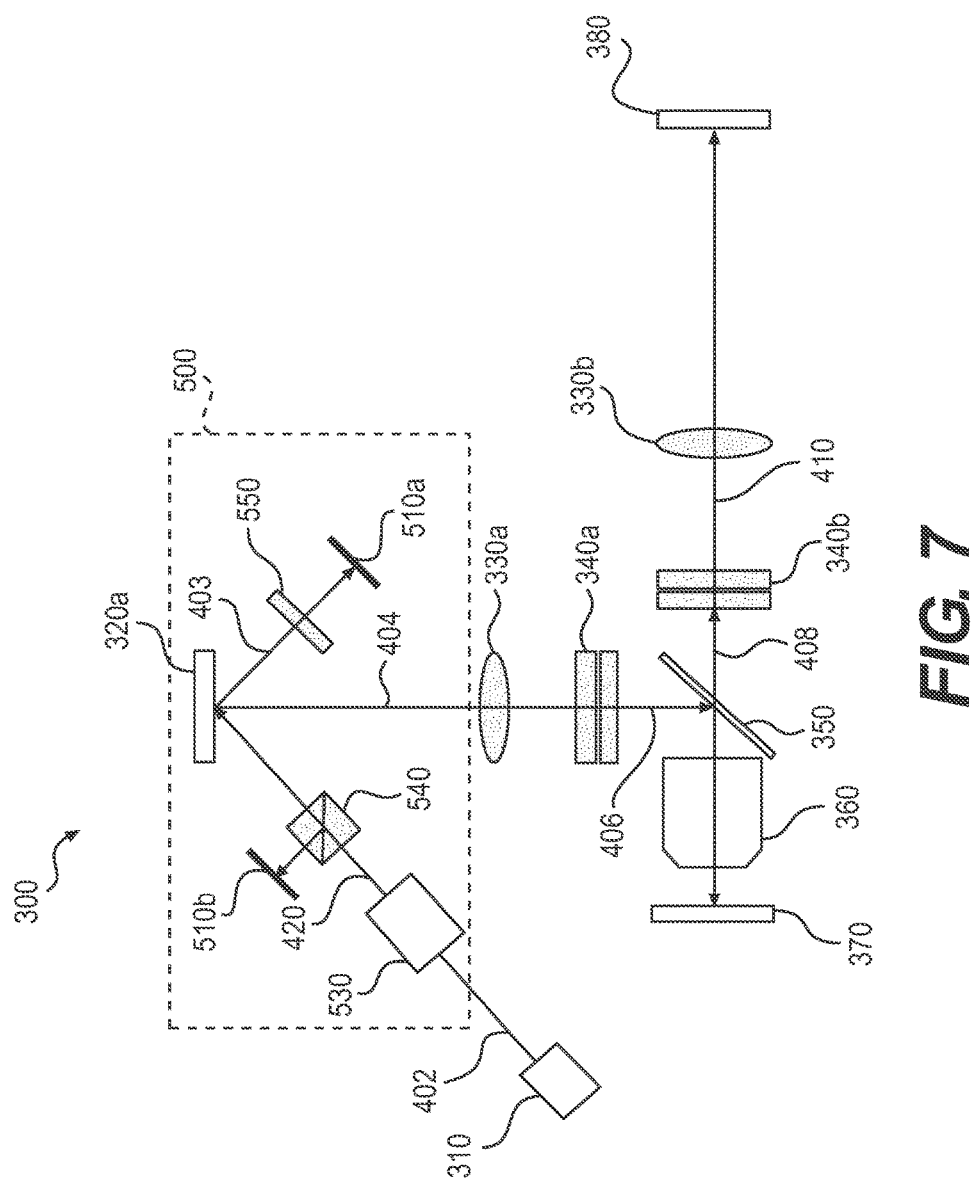
FIG. 7 is a schematic representation of another exemplary hyperspectral imaging system, according to embodiments of the present disclosure.

To solve the above-described technical problem for recycling excitation light 402 having discrete wavelengths or narrow spectra bands, in some embodiments, excitation light recycling system 500 may use a polarization-based scheme as shown in FIG. 7.

As shown in FIG. 7, polarization-based recycling system 500 may include one or more optical components. For example, recycling system 500 may include an optical isolator 530, a polarizing beamsplitter (PBS) 540, a quarter-wave plate (QWP) 550, and one or more mirrors, e.g., a first mirror 510a and a second mirror 510b. In some embodiments, optical isolator 530 may include a linear polarizer or may be optionally replaced by a linear polarizer.

In this scheme, optical isolator 530 allows the propagation of excitation light 402 in only one forward direction. Excitation light 402 may be a linearly polarized light, or may become linearly polarized after passing through optical isolator 530. The linearly polarized excitation light after passing through optical isolator 530 is referred to as excitation light 420. PBS 540 may be configured to transmit light having a vibration orientation parallel with that of excitation light 420 and reflect light having a vibration orientation orthogonal to that of excitation light 420. For example, excitation light 420 may be horizontally polarized or have a vibration orientation in a horizontal direction. PBS 540 may transmit horizontally polarized light and reflect vertically polarized light. Therefore, excitation light 420 transmits through PBS 540 and propagates towards SLM 320a.

Description below of the polarization-based scheme of recycling system 500 uses excitation light 420 that is horizontally polarized as an example. Embodiments of the polarization-based scheme of recycling system 500 is equally applicable for linearly polarized excitation light 420 having any vibration orientation.

As described above, when SLM 320a is a DMD, a small fraction of excitation light 420 may be reflected by the "on" micromirrors of the DMD towards lens 330a along the optical axis, while the off-axis excitation light 403 reflected by the "off" pixels are steered away from the optical axis. Mirror 510a may be configured to intercept the off-axis excitation light 403 and reflect it back to the "off" pixels on the DMD. Off-axis excitation light 403 may pass through QWP 550 a first time when it propagates towards mirror 510a and a second time when it is directed back to the DMD by mirror 510a, which rotate the vibration orientation of off-axis excitation light 403 by 90°. For example, horizontally polarized excitation light 403 may be changed to be vertically polarized after passing through QWP 550 twice. The vertically polarized excitation light is then reflected by the "off" micromirrors of the DMD towards PBS 540.

Because the vertically polarized excitation light reflected to PBS 540 has a vibration orientation orthogonal to that of horizontally polarized excitation light 420, it is reflected by PBS 540 and directed to mirror 510b. Without changing its vibration orientation, mirror 510b and PBS 540 then reflect the vertically polarized excitation light back to the DMD, where the "on" micromirrors then reflect the vertically polarized excitation light towards lens 330a along the optical axis. The "off" micromirrors reflect the vertically polarized excitation light, which again transmits through QWP 550 and mirror 510a twice and becomes horizontally polarized. This horizontally polarized excitation light would pass through PBS 540, but would not propagate back to light source 310 because of optical isolator 530.

In the above-described polarization-based scheme of recycling system 500, because QWP 550 rotates the vibration orientation of off-axis excitation light 403 by 90°, excitation light 404 reflected towards the optical axis, which includes the portion of the off-axis excitation light 403 that is recycled, would have orthogonal polarizations. In such instances, rather than a polarizing beamsplitter, beamsplitter 350 may suitably be a multiband dichroic that has multiple cut-off wavelengths and passbands. As described above, the multiband dichroic may be selected such that wavelengths of excitation light 402 having a discrete spectrum are substantially reflected and wavelengths of emitted fluorescent light 408 are substantially transmitted. Therefore, this polarization-based scheme may work better in systems 300 using a light source 310 having discrete wavelengths or narrow spectra bands, such as a combination of a set of lasers operating at discrete wavelengths.

Confocal Optical Sectioning Capability

As described above, system 300 may allow for confocal optical sectioning, which allows for selecting the depth of a focal plane in the sample. The depth of the focal plane may be selected by introducing one or more optical pinholes at a plane conjugate to the selected focal plane.

Figure 8:
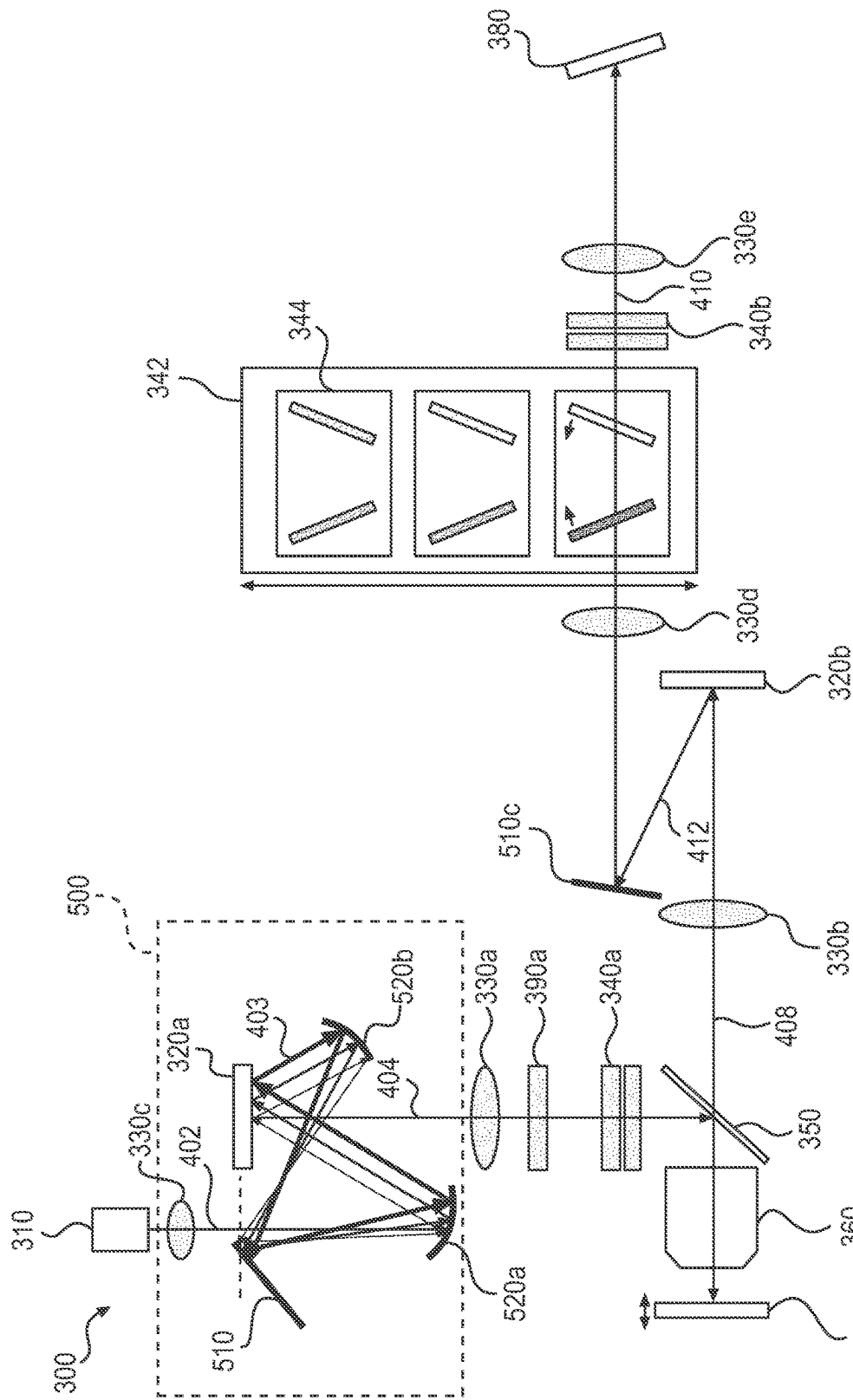
FIG. 8 is a schematic representation of another exemplary hyperspectral imaging system, according to embodiments of the present disclosure.

FIG. 8 is a schematic representation of an exemplary system 300 that allows for confocal optical sectioning. As shown in FIG. 8, system 300 may include the first SLM 320a for generating excitation pattern 100 as described above, a second SLM 320b for confocal optical sectioning, at least one additional mirror 510c, one or more tube lenses, e.g., 330d and 330e, and a z-axis translation stage or a tunable liquid lens (not shown). SLM 320b may have similar types and features as described above for SLM 320a. For example, pixels of SLM 320b may be individually modulated in the same manners as those described for SLM 320a.

SLM 320b may be placed at about a plane conjugate to a focal plane located at a desired depth in the sample along the optical axis. For example, lens 330b and objective 360 may form an imaging configuration. As shown in FIG. 8, lens 330b may be located behind objective 360 and SLM 320b may be located about one focal length behind lens 330b. The space between the back aperture of objective 360 and lens 330b is a collimated space, which may be adjusted as need based on various factors, such as the geometry of system 300 and a desired location of a minimum beam aperture. In some embodiments, lens 330b is placed about one focal length behind objective 360.

Pixels of SLM 320b may be selectively actuated or switched to "on" or "off" states to form a pinhole pattern matching or conjugating excitation pattern 100 on the sample. The pinhole pattern may include a plurality of artificial optical pinholes at the conjugate plane and reject out-of-focus fluorescent light from the sample. Therefore, out-of-focus fluorescent light would not pass through the detection system and are substantially removed or eliminated from the acquired 2-D image 200.

The size and separations of the artificial pinholes in the pinhole pattern are programmable, and may be customized based on the magnification of the imaging configuration formed by objective 360 and lens 330b. In some instances, the pinhole pattern may include a plurality of "on" pixels in elongated shapes to allow fluorescent light emitted from multiple locations on the sample (e.g., areas excited by excitation spots 112a-112f) to be acquired simultaneously. In other instances, the pinhole pattern may include an array of "on" pixels that match the size of the excitation lines or excitation spots in excitation pattern 100.

The fluorescent light 412 reflected by the "on" pixels of SLM 320b is then imaged to imaging device 380 by tube lenses 330d and 330e. For example, mirror 510c may be placed at a suitable position along the optical axis and for directing fluorescent light 412 reflected by the "on" pixels to the tube lenses. Tube lens 330d may be located about one focal length beyond the image produced by lens 330b (e.g., about one focal length behind SLM 320b) such that it re-collimates the fluorescent light from the sample. Imaging device 380 may be located about one focal length behind tube lens 330e or at a conjugate plane of SLM 320b. Because the fluorescent light is collimated in the space between tube lenses 330d and 330e, the distance between tube lenses 330d and 330e may be adjusted as desired. In some embodiments, tube lens 330e may be about two focal lengths behind tube lens 330d such that a plane midway between tube lens 330d and 330e is conjugate to an exit pupil of system 300.

By digitally changing and/or laterally shifting excitation pattern 100 and the matching pinhole pattern on SLM 320b correspondingly, the whole field of view may be scanned for acquiring a confocal-imaging dataset. By further scanning the field of view across the sample, the whole sample can be scanned to obtain a complete confocal-imaging dataset of the sample.

In some embodiments, imaging device 380 may be suitably tilted to reduce aberrations and thus improve the quality of the acquired 2-D image dataset. This is at least because the "on" pixels of SLM 320b direct fluorescent light 412 at an angle that is not perpendicular to the surface plane of SLM 320b such that an image plane formed by tube lenses 330d and 330e may be tilted. Aberrations caused by this tilting effect may be compensated by properly tilting imaging device 380. Aberrations may be further reduced if a dispersion angle of dispersive element 340b is adjusted to be parallel to a rotation axis of the tilted imaging device 380.

To change or select a depth of the focal plane, in some embodiments, sample holder 370 may be installed on the z-axis translation stage. The desired depth of the focal plane may be selected by moving sample holder 370 along the optical axis using the z-axis translation stage. Alternatively, objective 360 may be installed on the z-axis translation stage and the desired depth of the focal plane may be selected by moving objective 360 along the optical axis. As describe herein, the z-axis translation stage may also include x-y translation capability to move the field of view of system 300 across the sample in lateral directions. In other embodiments, the desired depth of the focal plane may be selected by tuning the focus of a tunable liquid lens (not shown) placed behind objective 360. Additionally, the z-translation stage or the tunable liquid lens may be controlled by a computer program to achieve autofocusing.

Advantageously, a degree of confocality may be adjusted as needed by changing the size and/or separation of the artificial pinholes formed by SLM 320b. For example, increasing the sizes of the pinholes by increasing the number of pixels in the pinholes and/or reducing the pinhole spacing may reduce the degree of confocality and thus the degree of depth selectivity of the desired focal plane. On the other hand, decreasing the size of the pinholes by reducing the number of pixels in the pinholes and/or increasing the pinhole spacing may increase the degree of confocality and thus the degree of depth selectivity of the desired focal plane. In some embodiments, the depth selectivity may be proportional to the ratio of the number of "off" and "on" pixels of SLM 320b. Therefore, SLM 320b may advantageously allow for switching between wide-field and confocal imaging as desired by conveniently adjusting the pinhole size and/or separation.

Additionally, the pinhole pattern formed by pixels of SLM 320b advantageously allows for confocal imaging of a plurality of areas on the sample simultaneously illuminated by excitation pattern 100. This may increase the speed and/or throughput of acquiring hyperspectral-imaging datasets across the sample at the desired focal plane comparing to traditional confocal microscopes that use sequential point-by-point scanning.

As shown in FIG. 8, in embodiments of system 300 using SLM 320b, dispersive element 340b may be located in the collimated space between tube lenses 330d and 330e. Because the pinhole pattern on SLM 320b matches excitation pattern 100 on the sample, fluorescent light 412 reflected by the artificial pinholes of SLM 320b can be dispersed by dispersive element 340b as described above such that the fluorescence emission spectra corresponding to the excitation spots of excitation pattern 100 can be acquired by the 2-D sensor of imaging device 380.

Selective Filtering of Fluorescence Emission Spectrum

In some applications, different fluorophores having fluorescence emission spectra that are spaced apart, such as green and red fluorophores, may be used or exist in the sample. This may result in lateral gaps in a fluorescence emission spectrum acquired in 2-D image 200 along the emission wavelength axis, resulting in inefficient use of the space on the 2-D sensor of imaging device 380.

In other applications, the combination of different fluorophores may result in an overall broad fluorescence emission spectrum to be acquired by imaging device 380. In some instances, multiple spectral regions within the broad emission fluorescence spectrum may be more useful than other regions. Acquiring the complete broad fluorescence emission spectrum may result in inefficient use of the space on the 2-D sensor of imaging device 380 and further reduce the throughput of acquiring the hyperspectral-imaging dataset.

To increase the efficiency of using the sensor space of imaging device 380 and increase the throughput of system 300, a spectral slicing system 342 may be included at a collimated space along the optical axis in the detection system. For example, as shown in FIG. 8, spectral slicing system 342 may be located between tube lenses 330*d* and 330*e*, and may be placed before dispersive element 340*b* in the detection system. Spectral slicing system 342 may selectively pass one or more spectral bands with tunable bandwidths and/or center wavelengths, thereby allowing for acquiring a hyperspectral-imaging dataset with desired spectral bands and/or desired spectral resolutions.

As shown in FIG. 8, spectral slicing system 342 may include a plurality of spectral slicing modules 344. Fluorescent light 408 emitted by the sample may enter spectral slicing system 342 after being collimated or re-collimated. Using one or more beamsplitters and/or motorized flip mirrors, spectral slicing system 342 may split an input collimated fluorescent light beam into one or more beams, each having a different spectral band, and direct them through spectral slicing modules 344 respectively. Each spectral slicing module 344 may filter one of the beams to have a desired bandwidth and a center wavelength. After the filtering, spectral slicing system 342 may combine the filtered beams into an output beam using one or more beamsplitters and/or motorized flip mirrors.

Spectral slicing modules 344 may each operate as a tunable bandpass filter with a tunable passband width and/or a tunable center wavelength. For example, spectral slicing module 344 may include a long-pass filter and a short-pass filter along its optical axis. At least one of the long-pass filter and short-pass filter is rotatable relative to the optical axis. Rotating the filters may adjust the angle of incidence of the beam on the filters and thus shift the wavelengths of their absorption or reflection edges. Thus, rotating the long-pass filter and/or short-pass may tune the bandwidth and/or center wavelength of the spectral passband formed by the long-pass and shot-pass filters. Alternatively, spectral slicing modules 344 may each include a tunable bandpass filter whose passband may be tuned by rotating the filter and thus tuning the angle of incidence of the beam on the filter.

Spectral slicing system 342 allows the measured fluorescence emission spectra to be adjustably filtered to desired spectral ranges useful for a particular application. By selecting the desired spectral ranges, the space on the 2-D sensor of imaging device 380 can be used more efficiently. For example, as described above, the degree of dispersion caused by dispersive element 340*b* can be adjustable. The spectral resolution of the selected spectral ranges of the fluorescence emission spectra may be increased by increasing the degree of spectral dispersion using dispersive element 340*b*, thereby providing more information of the fluorophores or fluorescent molecules in the sample.

Additionally, selecting the desired spectral ranges may allow for reducing the lateral spacing between the fluorescence emission spectra in 2-D image 200 along the emission wavelength axis, thereby improving the throughput of dataset acquisition. For example, by reducing the period of excitation pattern 100 in the horizontal direction, and decreasing the degree of spectral dispersion using dispersive element 340*b*, the period of the array of fluorescence emission spectra in the horizontal direction in 2-D image 200 may be reduced. This may in turn increase the number of fluorescence emission spectra that can be acquired in one exposure, thereby increasing the efficiency of using the senor space of imaging device 380.

Alternative Configurations

In some applications, more compact configurations of system 300 may be desirable. In such instances, system 300 may use diffractive elements in place of SLM 320*a* and/or SLM 320*b*. Embodiments of such configurations of system 300 are described below in reference to FIGS. 9-13.

Figure 9:
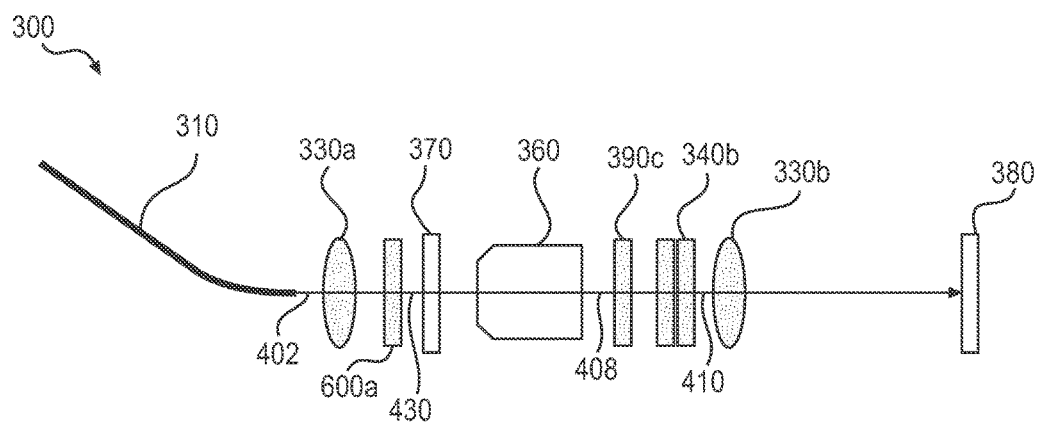
FIG. 9 is a schematic representation of another exemplary hyperspectral imaging system, according to embodiments of the present disclosure.

FIG. 9 is a schematic representation of an exemplary compact embodiment of system 300. As shown in FIG. 9, system 300 may advantageously use a transmission-type illumination to simplify its geometry. However, reflection-type illumination configurations as shown in FIGS. 3-8 may also be used depending on the application. In the illumination system, excitation light 402 from light source 310, such as a supercontinuum laser source provided through an optic fiber, is collimated by lens 330*a*, transmits through a first diffractive element 600*a*, and then illuminates a sample placed on sample holder 370. Diffractive element 600*a* modulates the phase of excitation light 402 transmitting through it and structures excitation light 402 for generating excitation pattern 100. The phase modulation may render a plurality of wavelets of the transmitted excitation light 430 with different directions and/or phases, generating a diffraction pattern in the far field. The diffraction pattern focused on the sample is referred to as excitation pattern 100.

Figure 12:
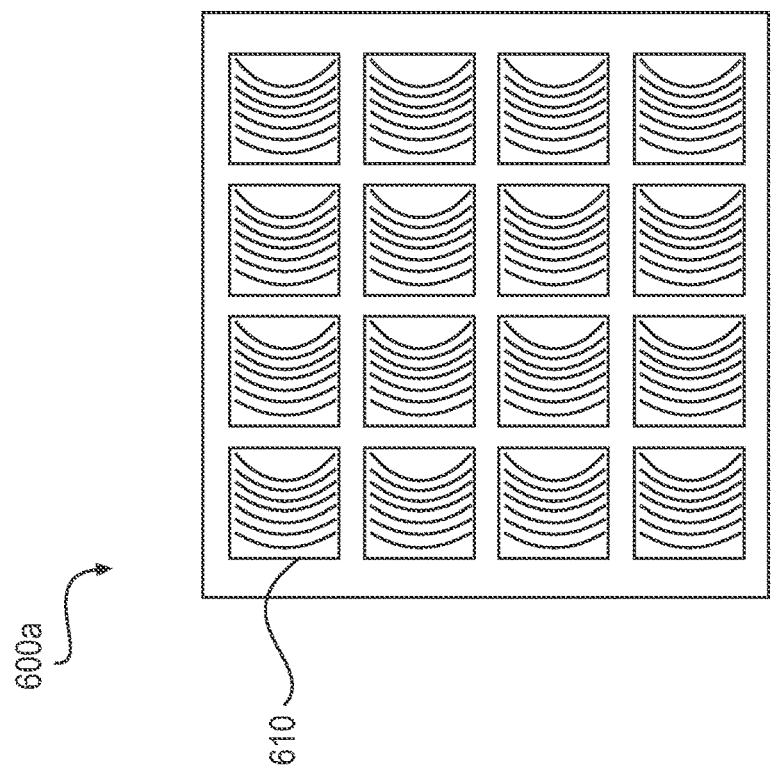
FIG. 12 is a schematic representation of an exemplary diffractive element, according to embodiments of the present disclosure.

FIG. 12 is a schematic representation of an exemplary diffractive element 600*a*. As shown in FIG. 12, in some embodiments, diffractive element 600*a* may be a 2-D array of diffractive lenses 610. For excitation light 402 having a single wavelength, diffractive element 600*a* generates a 2-D array of excitation spots, one by each diffractive lens 610. For excitation light 402 having multiple discrete wavelengths or a range of wavelengths, different wavelengths of excitation light 402 are diffracted by each diffractive lens 610 into several beams travelling in different angular directions. Therefore, when focused on the sample, the different wavelengths of excitation light 402 may have focuses spatially shifted from one another in a first lateral direction (e.g., vertical direction), thereby generating excitation pattern 100 as shown in FIG. 1 or FIG. 2.

In some embodiments, diffractive lenses 610 of diffractive element 600*a* may be zone plates that have transparent and nontransparent bands, conventional gratings made by, e.g., binary lithography, grayscale lithography, or molding processes, or subwavelength gratings made by binary lithography. In other embodiments, diffractive element 600*a* may be replaced with a 2-D lenslet array and a transmissive diffraction grating that have the phase modulation capability for generating excitation pattern 100 as described above.

In the detection system, fluorescent light 408 emitted by the sample is collected and collimated by objective 360, transmits through dispersive element 340*b*, and is then focused onto imaging device 380 by lens 330*b*. Dispersive element 340*b* may spectrally disperse fluorescence light 408 in a second lateral direction (e.g., horizontal direction) as described above. Dispersive element 340*b* may have the same features and functions as described above.

In some embodiments, system 300 may include a second linear polarizer 390*c*. Fluorescent light 408 may pass through polarizer 390*c*. When excitation light 402 is linearly polarized, polarizer 390*c* may be used to substantially reflect the polarized excitation light and thus block it from reaching imaging device 380. In other embodiments, a set of notch filters or a single multi-notch filter (not shown) may be added to the detection system along the optical axis.

Because diffractive element 600*a* does not have the digital programmability as that of an SLM, either diffractive element 600*a* or sample holder 370 may be translated in spatial dimensions to scan excitation pattern 100 across the field of view or the sample to obtain a complete 4-D hyperspectral-imaging dataset. The scanning scheme may be the same as described above in reference to FIGS. 1 and 2. Different areas in each scanning cell 110 may be illuminated by spatially shifting excitation pattern 100 in the vertical and horizontal directions. At each spatial position of excitation pattern 100, at least one 2-D image 200 of fluorescence emission spectra of the illuminated areas can be acquired. Then, a plurality of 2-D images 200 of fluorescence emission spectra can be acquired corresponding to a series of excitation patterns 100 laterally shifted from one another and used for reconstructing the 4-D hyperspectral-imaging dataset.

Figure 10:
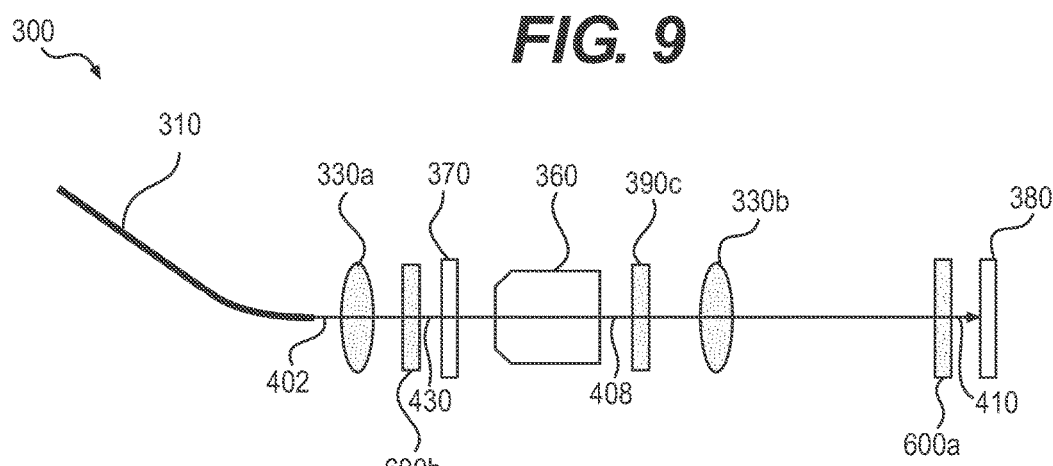
FIG. 10 is a schematic representation of another exemplary hyperspectral imaging system, according to embodiments of the present disclosure.

FIG. 10 is a schematic representation of another exemplary compact embodiment of system 300. System 300 as shown in FIG. 10 may allow for acquiring a 4-D hyperspectral-imaging dataset by performing scanning in one lateral direction. For example, system 300 may include diffractive element 600a in the detection system and another diffractive element 600b in the illumination system. As shown in FIG. 10, in the illumination system, excitation light 402 from light source 310 is collimated by lens 330a, transmits through diffractive element 600b, and then illuminates a sample placed on sample holder 370.

Figure 13:
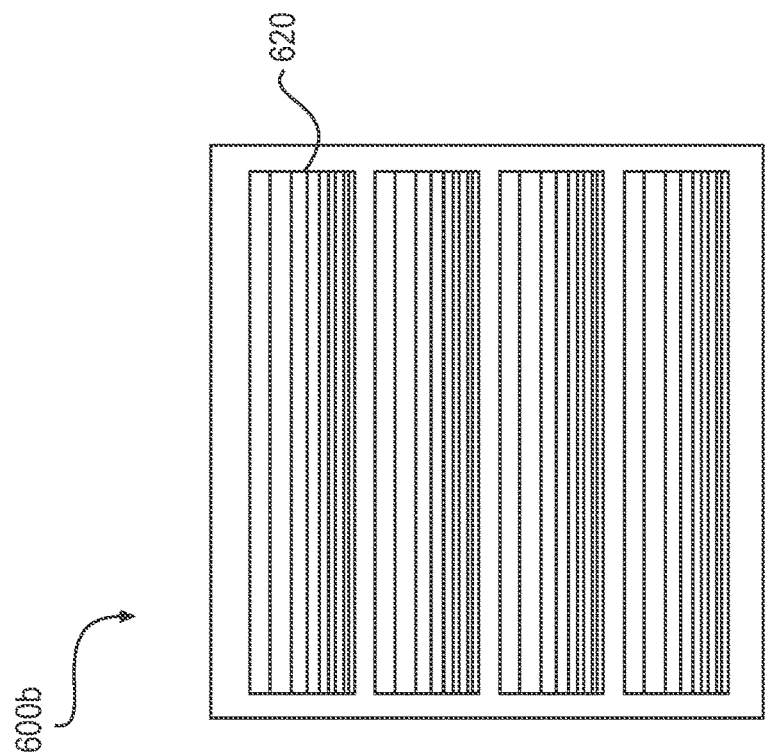
FIG. 13 is a schematic representation of another exemplary diffractive element, according to embodiments of the present disclosure.

FIG. 13 is a schematic representation of an exemplary diffractive element 600b. Diffractive element 600b may modulate the phase of excitation light 402 transmitting through it and render wavelets of transmitted excitation light 430 having different directions and/or phases. In some embodiments, diffractive element 600b may include a linear array of diffractive cylindrical lenslets 620. For excitation light 402 of a single wavelength, diffractive element 600b generates a repeating pattern of single-colored stripes, one by each cylindrical lenslet 620. For excitation light 402 having multiple discrete wavelengths or a range of wavelengths, different wavelengths of excitation light 402 are diffracted by each cylindrical lenslet 620 into several beams travelling in different angular directions. Therefore, when focused on the sample, different wavelengths of excitation light 402 may have focuses spatially shifted from one another in a first lateral direction (e.g., vertical direction), generating a repeating pattern of a series of shifted different-colored stripes. Depending on the spectrum of light source 310, the different-colored stripes may be connected or separated in the first lateral direction. The repeating pattern of shifted different-colored stripes are then illuminated on the sample.

In the detection system, rather than using dispersive element 340b, diffractive element 600a may be added and placed in front of imaging device 380. Fluorescent light 408 emitted by the sample is collected and collimated by objective 360, transmits through polarizer 390c, and is then imaged onto diffractive element 600a by lens 330b. Diffractive lenses 610 of diffractive element 600a may then spectrally disperse the fluorescent light in a second lateral direction (e.g., horizontal direction) and image the spectrally dispersed fluorescent light 410 to the 2-D sensor of imaging device 380.

In some embodiments, the focal length of lens 330b is selected such that a diffraction-limited spot size of lens 330b at its focal plane may cover a plurality of pixels of the 2-D sensor of imaging device 380. This may affect the numerical aperture (NA), the focal ratio (f-ratio), and/or the magnification of lens 330b. For example, to increase the diffraction-limited spot size of lens 330b, lens 330b may have a longer focal length, a smaller NA or a larger f-ratio, and/or a greater magnification.

Diffractive element 600a may be designed or selected such that the diameters of its diffractive lenses 610 is about the size of a diffraction-limited spot of lens 330b. Different wavelengths of the fluorescent light 410 deflected and focused by each diffractive lens 610 may have focuses spatially shifted from one another in the second lateral direction, generating an array of fluorescence emission spectra as shown in FIG. 1 or FIG. 2.

Embodiments of system 300 as shown in FIG. 10 allows for acquiring fluorescence emission spectra in a 2-D image 200 as shown in FIG. 1 or FIG. 2 for areas or locations on the sample illuminated by the repeating pattern of a series of laterally shifted different-colored stripes. To acquire the excitation spectra, the repeating pattern may be scanned along the first lateral direction such that the areas or locations on the sample previously illuminated by a colored stripe of the repeating pattern are illuminated by a different-colored stripe. The shifting of the repeating pattern in the first lateral direction and subsequent acquisition of a corresponding 2-D image 200 may be performed for a plurality times. In such instances, fluorescence emission spectra corresponding to the excitation wavelengths for each area or location on the sample can be acquired and used for reconstructing the 4-D hyperspectral-imaging dataset.

In the embodiments of system 300 as shown in FIG. 10, because the repeating pattern of a series of laterally shifted different-colored stripes is continuous in the second lateral direction, the repeating pattern may only need to be scanned along the first lateral direction to obtain the excitation spectra for all areas or locations within the field of view. This may further improve the throughput and efficiency of system 300 for acquiring the 4-D hyperspectral-imaging dataset.

Along the second lateral direction, each area illuminated by the continuous colored stripes can be imaged to a diffractive lens 610, which then disperses the fluorescent light and focuses it to imaging device 380. In such instances, the spatial resolution along the second lateral direction may depend on the size and focal length of diffractive lenses 610, the focal lengths of lens 330b and objective 360, and/or the size of the 2-D sensor of imaging device 380. In some embodiments, increasing the focal length of lens 330b may allow for using larger diffractive lenses 610. The spectral resolution along the second lateral direction may depend on the width and/or focal length of diffractive lenses 610, and the off-axis focal shifts generated by diffractive lenses 610 in the second lateral direction. For example, increasing groove density of diffractive lenses 610 would increase the diffraction angles of the fluorescent light and thus the off-axis focal shifts, thereby increasing the spectral resolution in the second lateral direction.

Figure 11:
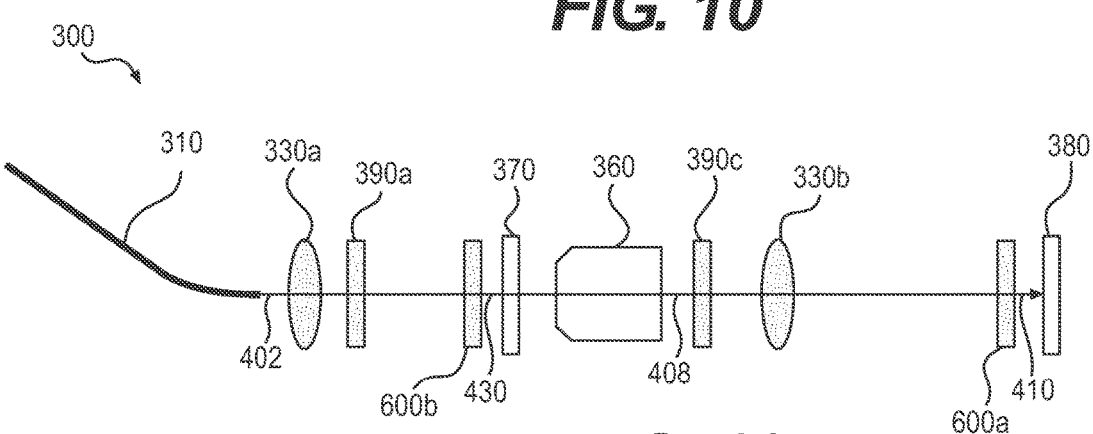
FIG. 11 is a schematic representation of another exemplary hyperspectral imaging system, according to embodiments of the present disclosure.

FIG. 11 is a schematic representation of another exemplary compact embodiment of system 300 that provides the capability for measuring fluorescence polarization. As shown in FIG. 11, system 300 may include two polarizers 390a and 390c. Polarizer 390a may be at a suitable place along the optical axis in the illumination system, thereby generating linearly polarized excitation light. Polarizer 390c may be at a suitable place along the optical axis in the detection system, thereby transmitting emitted fluorescent light 408 having a given vibration orientation. To perform fluorescence polarization assays, the transmission axis of polarizer 390c may be rotated between orientations parallel and orthogonal to the vibration orientation of the linearly polarized excitation light. 2-D images 200 of the fluorescence emission spectra of fluorescent light 408 having vibration orientations parallel to and orthogonal to that of the polarized excitation light may be respectively acquired by imaging device 380. The acquired 2-D images 200 may then be used for fluorescence polarization (or anisotropy) assay.

Figure 14:
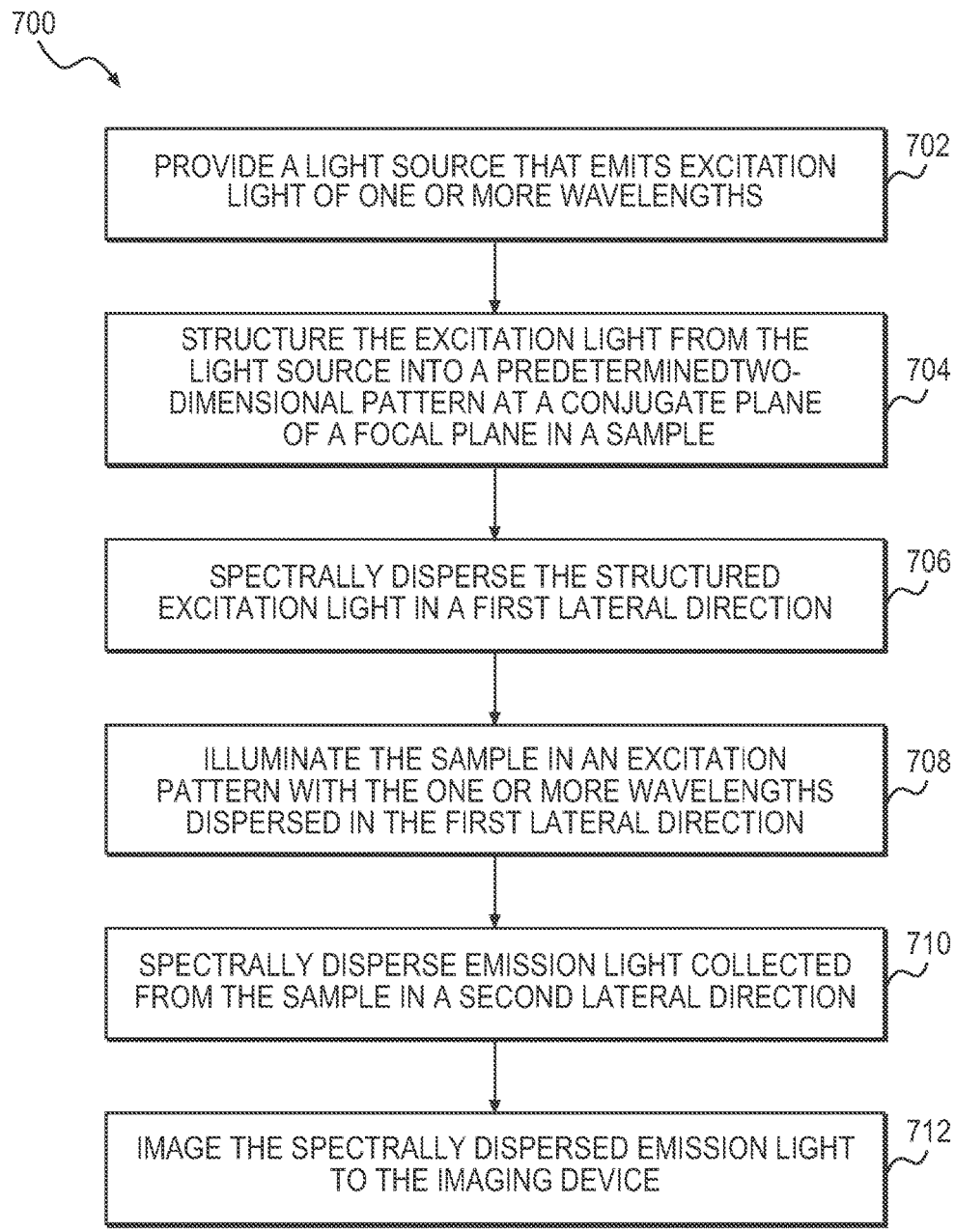
FIG. 14 is a flowchart of an exemplary method for hyperspectral imaging, according to embodiments of the present disclosure.

System 300 as described herein may be utilized in a variety of methods for hyperspectral imaging. FIG. 14 is a flowchart of an exemplary method 700 for performing hyperspectral imaging or for acquiring a hyperspectral-imaging dataset of a sample. Method 700 uses system 300 and features of the embodiments of system 300 described above in reference to FIGS. 3-13.

At step 702, light source 310 having a discrete spectrum or a continuous spectrum is provided and configured to emit excitation light 402 having one or more wavelengths. At step 704, excitation light 402 is structured by SLM 320a to into a predetermined two-dimensional pattern at a conjugate plane of a focal plane in the sample. At step 706, the structured excitation light, e.g., excitation light 404 reflected by SLM 320a, is spectrally dispersed by dispersive element 340a in a first lateral direction. At step 708, spectrally dispersed excitation light 406 is directed towards and focused on the sample, illuminating the sample in excitation pattern 100 with the one or more wavelengths dispersed in the first lateral direction. At step 710, fluorescent light 408 collected from the sample is spectrally dispersed by dispersive element 340b in a second lateral direction. At step 712, spectrally dispersed fluorescent light 410 is imaged to a 2-D sensor of imaging device 380.

Method 700 may further include additional steps. For example, method 700 may include calibrating system 300 before acquiring 2-D image 200. Various optical components in system 300 may be suitably calibrated and aligned such that focused 2-D images 200 with reduced or minimum distortion can be acquired.

Method 700 may further include polarizing excitation light 402 to be directed to the sample using a first polarizer, and substantially reflecting light collected from the sample having the same polarization as that of the polarized excitation light using a second polarizer or a polarizing beamsplitter (PBS).

Method 700 may further include illuminating the sample sequentially in a series of excitation patterns 100 laterally shifted from one another, and obtaining a plurality of 2-D images 200 of the spectrally dispersed emission light corresponding to the series of excitation patterns 100, and reconstructing the plurality of 2-D images 200 to provide a 4-D hyperspectral-imaging dataset. As described above, each 2-D image 200 records an array of fluorescence emission spectra corresponding to each laterally shifted excitation pattern 100.

Method 700 may further include providing programmable artificial optical pinholes at a plane conjugate to the focal plane by SLM 320b, forming a series of pinhole patterns by pixels of SLM 320b, and matching the series of pinhole patterns to the series of excitation patterns 100. As described above, light collected from SLM 320b is imaged to imaging device 380 using one or more lenses. A 2-D image 200 of the spectrally dispersed emission light may be acquired after each lateral shift of excitation pattern 100 and the formation of its matching pinhole pattern. Method 700 may further include reconstructing the 2-D images 200 corresponding to the series of excitation patterns 100 to provide a 4-D hyperspectral-imaging dataset of the selected focal plane of the sample.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware and software, but systems and methods consistent with the present disclosure can be implemented as hardware alone. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

Instructions or operational steps stored by a computer-readable medium may be in the form of computer programs, program modules, or codes. As described herein, computer programs, program modules, and code based on the written description of this specification, such as those used by the controller, are readily within the purview of a software developer. The computer programs, program modules, or code can be created using a variety of programming techniques. For example, they can be designed in or by means of Java, C, C++, assembly language, or any such programming languages. One or more of such programs, modules, or code can be integrated into a device system or existing communications software. The programs, modules, or code can also be implemented or replicated as firmware or circuit logic.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:
1. A hyperspectral imaging system, comprising:
a sample holder configured to hold a sample;
a light source configured to emit excitation light having one or more wavelengths;
a two-dimensional (2-D) imaging array; and an optical system comprising:
  a first spatial light modulator (SLM);
  a first spectral separator; and
  a second spectral separator;
  wherein the optical system is configured to (i) structure the excitation light, using the first SLM, into a predetermined two-dimensional excitation pattern at a conjugate plane of a focal plane in the sample; (ii) spectrally disperse, using the first spectral separator, the excitation pattern; (iii) use the excitation pattern to illuminate the sample with the one or more wavelengths dispersed along a first direction within the focal plane; (iv) collect, from the sample, emission light; (v) spectrally disperse, using the second spectral separator, the collected emission light; and (vi) provide the collected emission light in-focus to the imaging array such that the collected emission light is spectrally dispersed along a second direction.

2. The hyperspectral imaging system of claim 1, wherein the optical system further comprises an objective, wherein the objective focuses the excitation light and collimates the collected emission light.

3. The hyperspectral imaging system of claim 1, wherein the optical system further comprises an optical beamsplitter, wherein the optical beamsplitter directs the excitation light onto the sample and directs the collected emission light to the imaging array.

4. The hyperspectral imaging system of claim 1, wherein the optical system further comprises a first polarizer configured to polarize the excitation light.

5. The hyperspectral imaging system of claim 4, wherein the optical system further comprises at least one of a second polarizer or a polarizing beamsplitter (PBS) configured to reflect light having the same polarization as that of the polarized excitation light.

6. The hyperspectral imaging system of claim 1, wherein the first SLM comprises at least one of a digital micromirror device (DMD), a diffractive element, a liquid crystal device (LCD), or a liquid crystal-on-silicon (LCOS) device.

7. The hyperspectral imaging system of claim 1, further comprising a plurality of optics, wherein a selection of pixels of the first SLM directs a portion of the excitation light away from an optical axis of the hyperspectral imaging system, and wherein the plurality of optics recycle the portion of the excitation light that is directed away from the optical axis of the hyperspectral imaging system by the SLM.

8. The hyperspectral imaging system of claim 7, wherein the plurality of optics comprise at least one lens and at least one mirror, wherein the at least one lens and the at least one mirror of the plurality of optics direct and collimate the excitation light directed away from the optical axis of the hyperspectral imaging system back to the optical axis of the hyperspectral imaging system via one or more reflections.

9. The hyperspectral imaging system of claim 7, wherein the plurality of optics comprise a PBS, at least two plane mirrors, and a quarter-wave plate, wherein the PBS, the at least two plane mirrors, and the quarter-wave plate of the plurality of optics direct the excitation light directed away from the optical axis of the hyperspectral imaging system back to the optical axis of the hyperspectral imaging system via one or more reflections.

10. The hyperspectral imaging system of claim 1, wherein the optical system further comprises a second SLM, wherein pixels of the second SLM operate as programmable artificial optical pinholes to form a pinhole pattern that matches the excitation pattern at the plane conjugate of the focal plane, and wherein the optical system provides the collected emission light in-focus from the focal plane to the second SLM.

11. The hyperspectral imaging system of claim 1, wherein at least one of the first spectral separator or the second spectral separator comprises a diffraction grating or a prism.

12. The hyperspectral imaging system of claim 1, wherein the light source comprises at least one of a high-pressure mercury lamp, a xenon lamp, a halogen lamp, a metal halide lamp, a supercontinuum light source, a laser, or an LED.

13. The hyperspectral imaging system of claim 1, further comprising a controller operably coupled to the first SLM, the light source, and the imaging array, wherein the controller is configured to operate the first SLM to modulate pixels of the first SLM, to operate the light source, and to operate the imaging array.

14. The hyperspectral imaging system of claim 1, wherein the excitation pattern comprises an array of excitation spots or excitation stripes.

15. A method for hyperspectral imaging, comprising:
  providing, from a light source, excitation light with one or more wavelengths;
  structuring, by a first spatial light modulator (SLM), the excitation light from the light source into a predetermined two-dimensional excitation pattern at a conjugate plane of a focal plane in a sample;
  spectrally dispersing the excitation pattern;
  using the excitation pattern to illuminate the sample with the one or more wavelengths dispersed along a first direction within the focal plane;
  spectrally dispersing emission light collected from the sample; and
  imaging, using a two-dimensional (2-D) imaging array, the spectrally dispersed emission light, wherein the spectrally dispersed emission light is received in-focus by the imaging array such that the spectrally dispersed emission light is spectrally dispersed along a second direction.

16. The method of claim 15, further comprising
  polarizing, by a first polarizer, the excitation light; and
  reflecting, by at least one of a second polarizer or a polarizing beamsplitter (PBS), light having the same polarization as that of the polarized excitation light.

17. The method of claim 15, wherein the first SLM comprises at least one of a digital micromirror device (DMD), a diffractive element, a liquid crystal device (LCD), or a liquid crystal-on-silicon (LCOS) device.

18. The method of claim 15, wherein structuring, by the first spatial light modulator (SLM), the excitation light from the light source comprises directing a portion of the excitation light away from an optical axis of a hyperspectral imaging system including the light source, the first SLM, and the imaging array, wherein the method further comprises:
  recycling the portion of the excitation light that is directed away from the optical axis of the hyperspectral imaging system.

19. The method of claim 15, further comprising
  illuminating the sample sequentially in a series of excitation patterns that are shifted, within the focal plane within the sample, from each other;
  obtaining, using the imaging array, a plurality of 2-D images of the spectrally dispersed emission light, wherein each of the obtained 2-D images corresponds to a respective one of the excitation patterns in the series of excitation patterns; and
  reconstructing the obtained plurality of 2-D images to provide a 4-D hyperspectral-imaging dataset.

20. The method of claim 19, further comprising providing, by a second SLM, a series of patterns of artificial optical pinholes at a further plane that is conjugate to the focal plane, wherein each pattern of artificial optical pinholes in the series of patterns of artificial optical pinholes matches a corresponding excitation pattern in the series of excitation patterns.

* * * * *